US010668162B2

(12) United States Patent
Houthoff et al.

(10) Patent No.: US 10,668,162 B2
(45) Date of Patent: Jun. 2, 2020

(54) METHOD FOR PREPARING CELL TARGETING CONJUGATES, AND THE COMPLEXES OBTAINED

(71) Applicant: LinXis B.V., Breda (NL)

(72) Inventors: Hendrik Jan Houthoff, Amsterdam (NL); Augustinus A. M. S. Van Dongen, Utrecht (NL); Robbert Jan Kok, Nieuwegein (NL); Dennis Christian Johannes Waalboer, IJmuiden (NL); Sytze Jan Buwalda, Utrecht (NL); Niels Jurriaan Sijbrandi, Utrecht (NL)

(73) Assignee: LinXis B.V., Breda (NL)

( * ) Notice: Subject to any disclaimer, the term of this patent is extended or adjusted under 35 U.S.C. 154(b) by 399 days.

(21) Appl. No.: 14/370,742

(22) PCT Filed: Jan. 4, 2013

(86) PCT No.: PCT/NL2013/050003
§ 371 (c)(1),
(2) Date: Jul. 3, 2014

(87) PCT Pub. No.: WO2013/103301
PCT Pub. Date: Jul. 11, 2013

(65) Prior Publication Data
US 2014/0377174 A1    Dec. 25, 2014

(30) Foreign Application Priority Data

Jan. 6, 2012   (EP) .................................... 12150366

(51) Int. Cl.
| A61K 51/10 | (2006.01) |
| A61K 47/48 | (2006.01) |
| A61K 49/00 | (2006.01) |
| A61K 47/68 | (2017.01) |
| A61K 31/337 | (2006.01) |
| A61K 31/517 | (2006.01) |
| A61K 31/555 | (2006.01) |
| A61K 31/704 | (2006.01) |

(52) U.S. Cl.
CPC ...... *A61K 47/48561* (2013.01); *A61K 31/337* (2013.01); *A61K 31/517* (2013.01); *A61K 31/555* (2013.01); *A61K 31/704* (2013.01); *A61K 47/6803* (2017.08); *A61K 47/6849* (2017.08); *A61K 47/6855* (2017.08); *A61K 47/6869* (2017.08); *A61K 47/6889* (2017.08); *A61K 49/0032* (2013.01); *A61K 49/0058* (2013.01)

(58) Field of Classification Search
CPC .............. A61K 47/00; A61K 47/48561; A61K 47/48384; A61K 47/48584; A61K 47/48638; A61K 47/48715; A61K 31/00; A61K 31/704; A61K 31/337; A61K 31/517; A61K 31/555; A61K 49/00; A61K 49/0058; A61K 49/0032; A61K 47/6889; A61K 47/6849; A61K 47/6855; A61K 47/6803; A61K 47/6869; A61K 51/10
USPC ......... 424/1, 1.11, 1.65, 1.49, 1.69, 9.1, 9.2, 424/9.3, 9.4, 9.5, 9.6; 514/1, 1.1; 530/300; 534/7, 10–16
See application file for complete search history.

(56) References Cited

U.S. PATENT DOCUMENTS

| 5,714,327 A | 2/1998 | Houthoff et al. |
| 5,759,514 A * | 6/1998 | Mattes ............... A61K 51/1093 424/1.11 |
| 7,591,994 B2 * | 9/2009 | Govindan ........ A61K 47/48215 424/1.49 |
| 2009/0269279 A1 | 10/2009 | Chen |

FOREIGN PATENT DOCUMENTS

| WO | 02097439 A2 | 12/2002 |
| WO | 2007011217 A2 | 1/2007 |
| WO | 2013103301 A2 | 7/2013 |

OTHER PUBLICATIONS

Heetebrij et al, ChemBioChem., vol. 4, pp. 573-583. (Year: 2003).*
International Search Report for International Application No. PCT/NL2013/05003, dated Apr. 10, 2013, 8 pages.
Dolman, M.E.M. et al., "Drug targeting to the kidney: Advances in the active targeting of therapeutics to proximal tubular cells" Advance Drug Delivery Reviews, vol. 62, No. 14, 2010, pp. 1344-1357.
Fretz, M. et al., "Intervention in growth factor activated signaling pathways by renally targeted kinase inhibitors" Journal of Controlled Release, vol. 132, No. 3, 2008, pp. 200-207.
Haselberg, R et al., "Characterization of drug-lysozyme conjugates by sheathless capillary electrophoresis-time-of-flight mass spectrometry" Analytica Chimica Acta, vol. 698, No. 1, 2011, pp. 77-83.
International Written Opinion for International Application No. PCT/NL2013/050003, dated Jul. 15, 2013, 12 pages.
Japanese Notice of Reasons for Refusal for Japanese Application No. 2014-551220, dated Aug. 10, 2016, 6 pages with English Translation.

(Continued)

*Primary Examiner* — D. L. Jones
(74) *Attorney, Agent, or Firm* — TraskBritt

(57) ABSTRACT

A first aspect of the disclosure relates to a method for preparing cell-targeting conjugates by coupling at least one functional moiety, such as a therapeutic compound, diagnostic compound or chelating agent to a targeting moiety. A second aspect of this disclosure relates to the cell-targeting conjugates obtainable with this method. A third aspect of the disclosure described herein relates to pharmaceutical compositions comprising the cell-targeting conjugates.

7 Claims, 12 Drawing Sheets

(56) References Cited

OTHER PUBLICATIONS

Japanese Notice of Reasons for Refusal for Japanese Application No. 2014-551220, dated Oct. 13, 2015, 11 pages with English Translation.

* cited by examiner

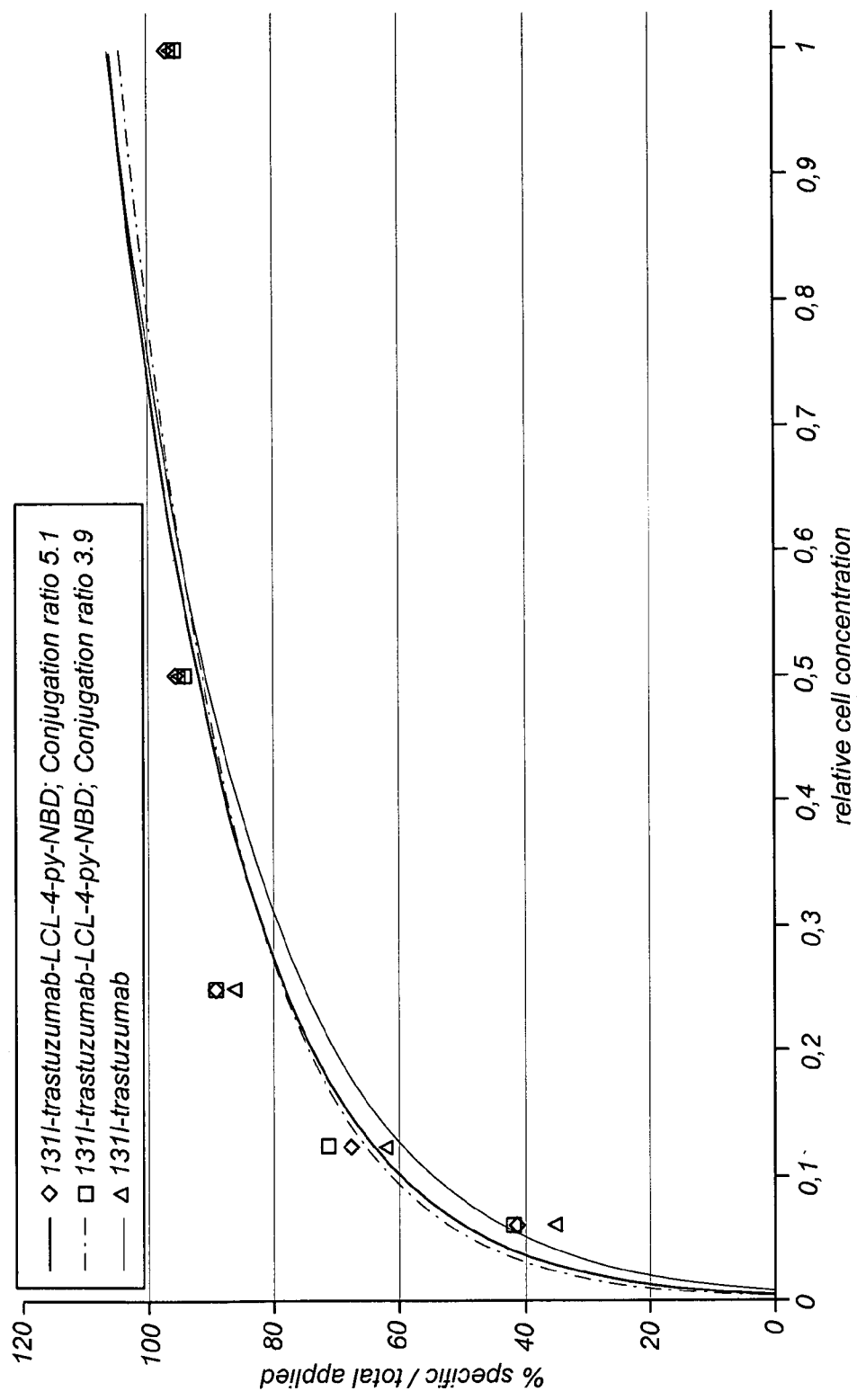
Fig. 1.1

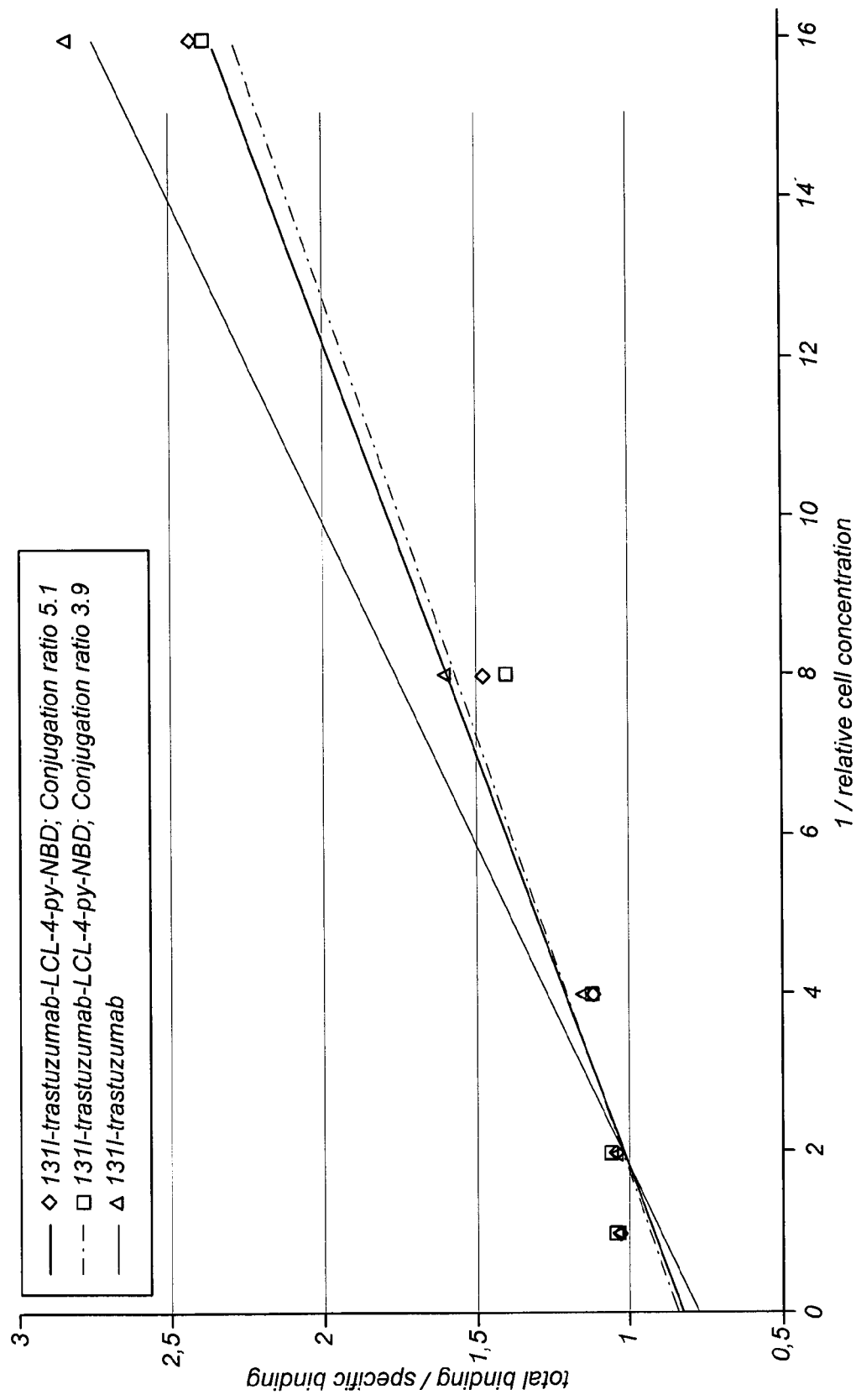
Fig. 1.2

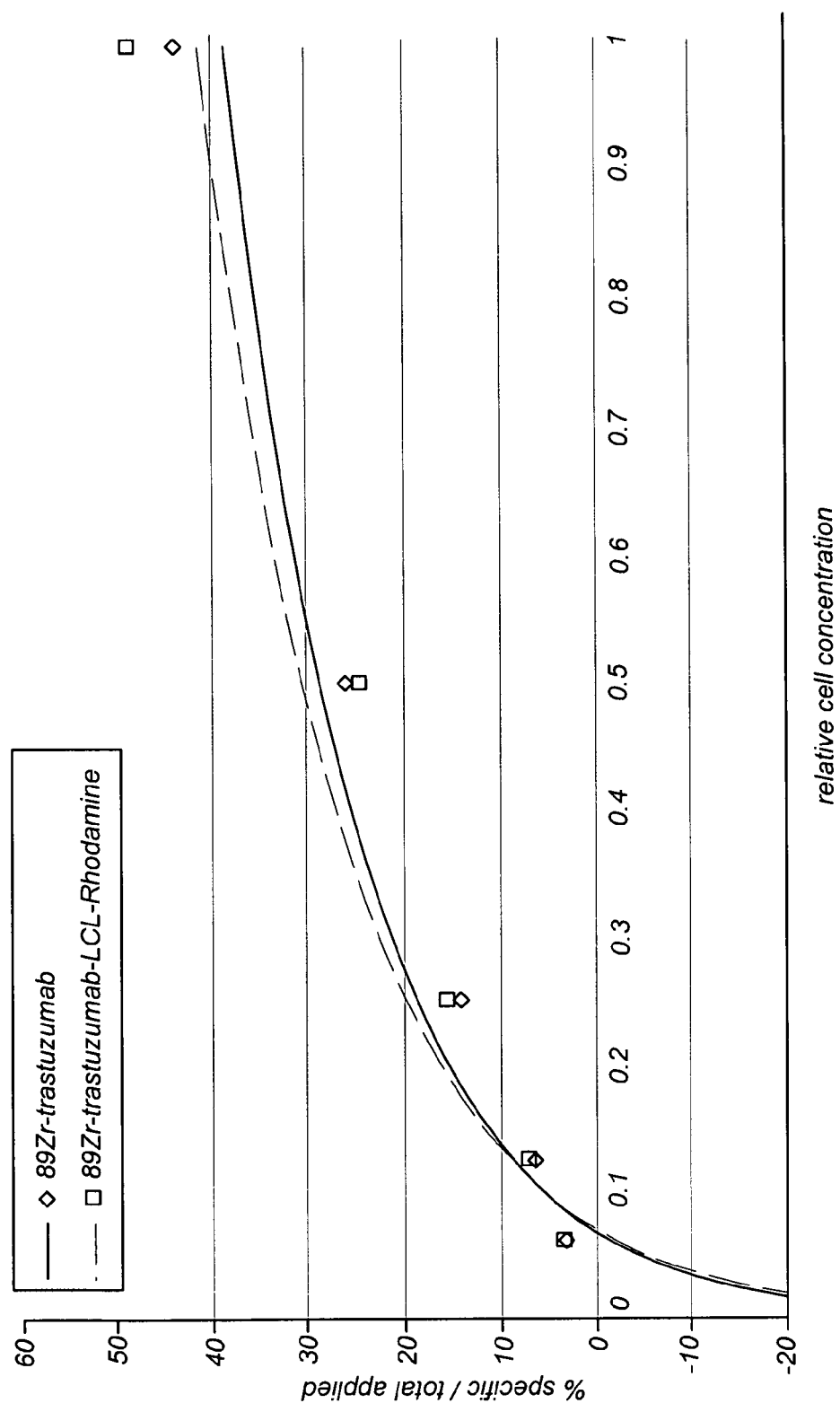
Fig. 2.1

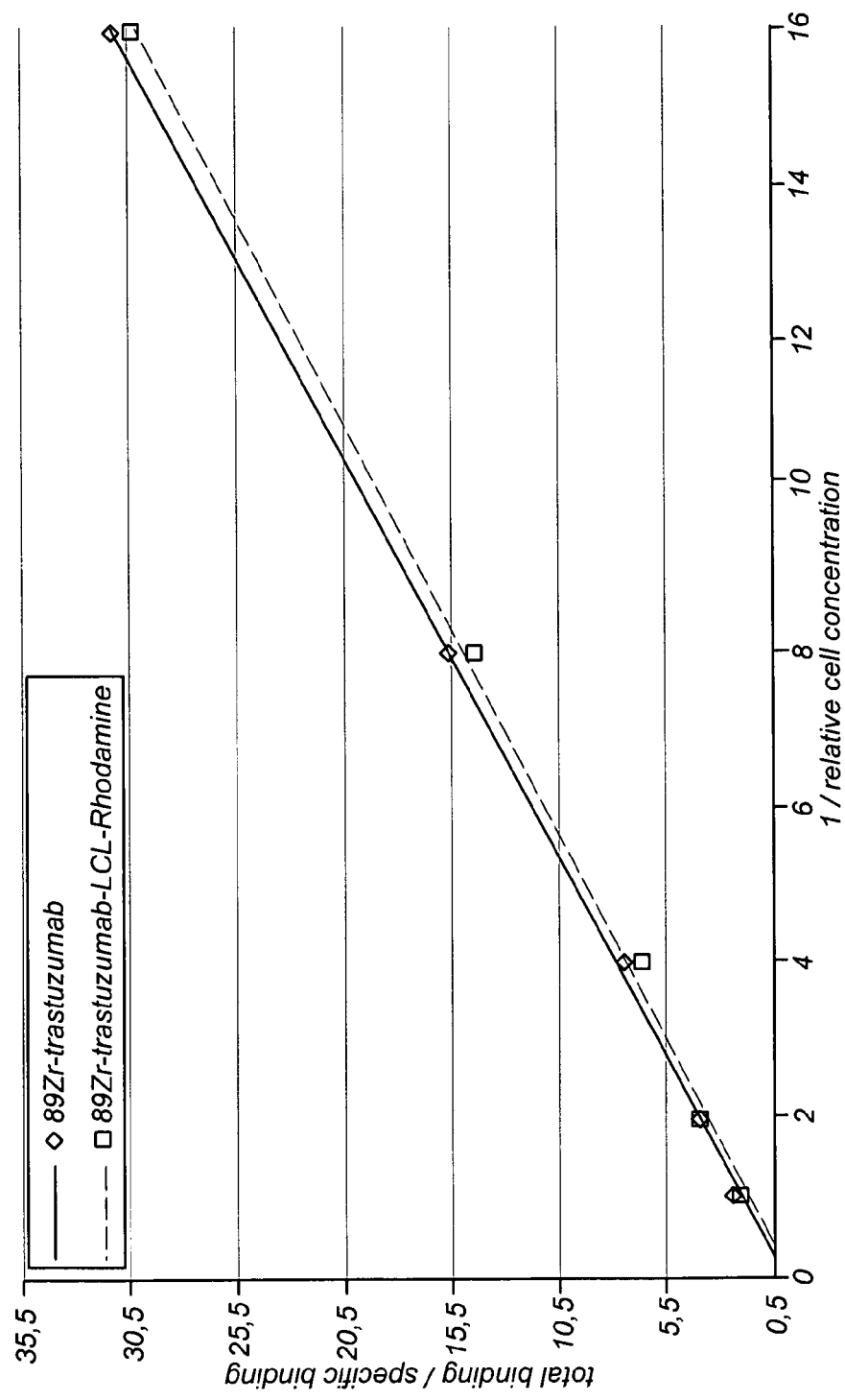
Fig. 2.2

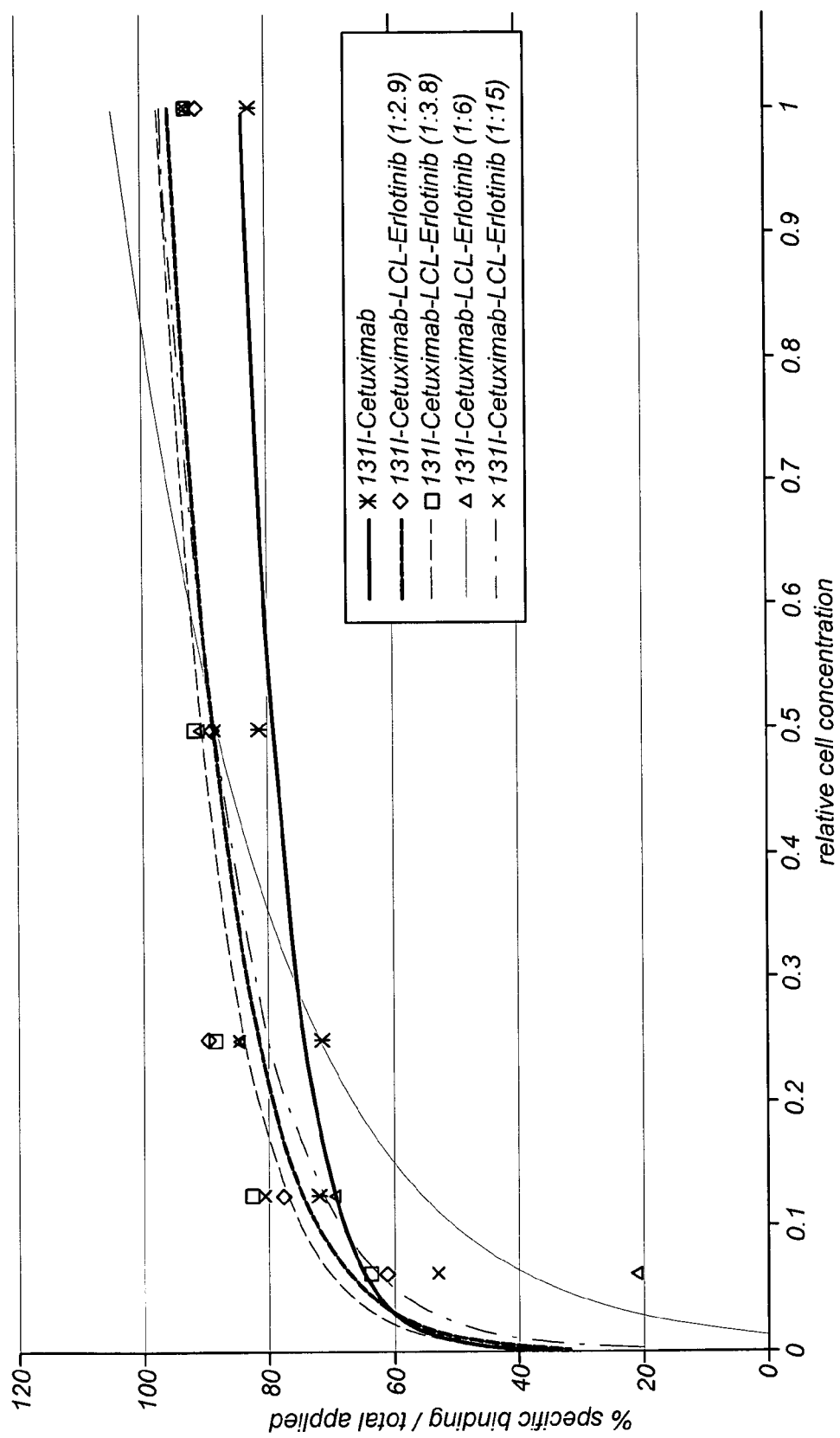
Fig. 3.1

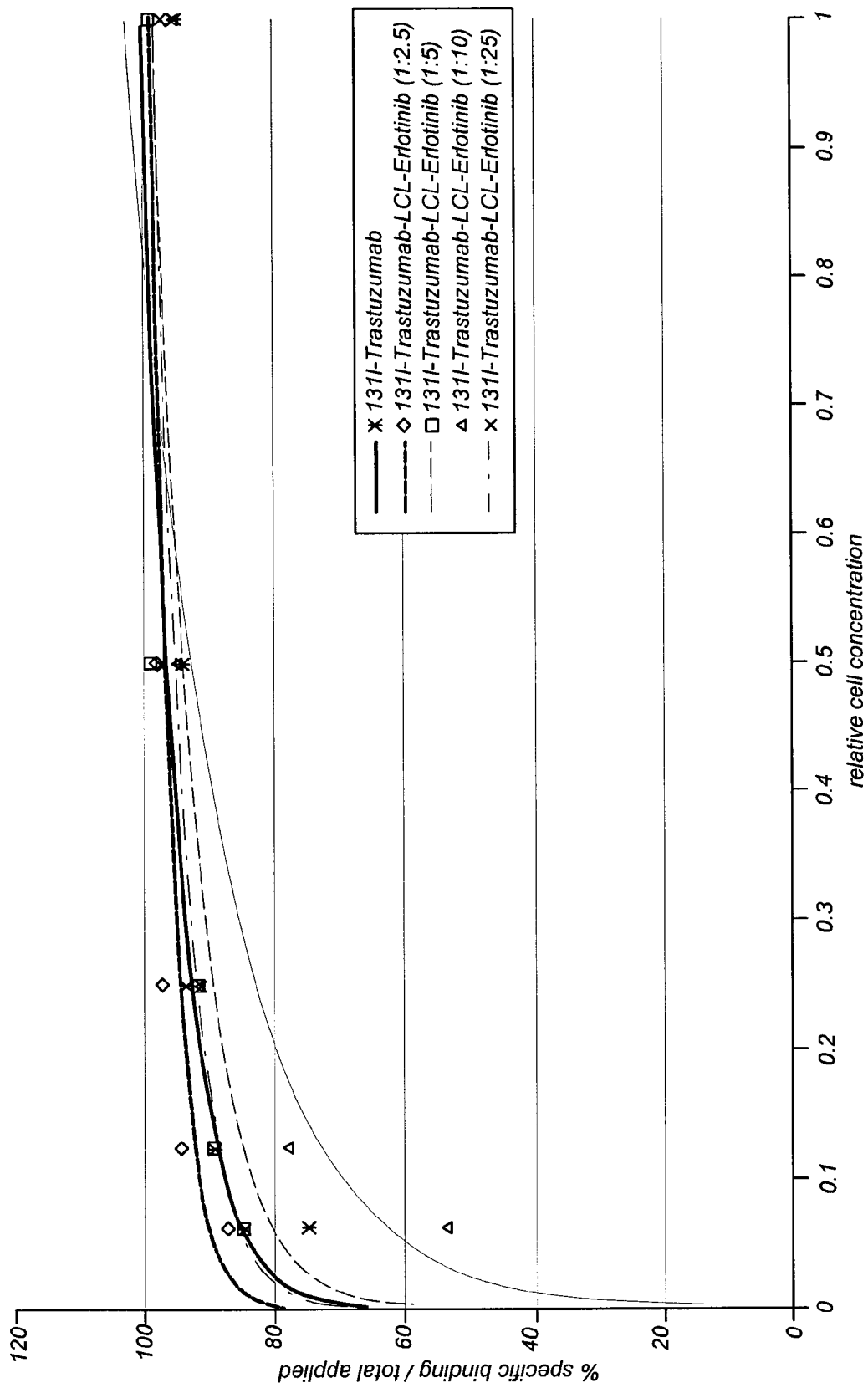
Fig. 3.2

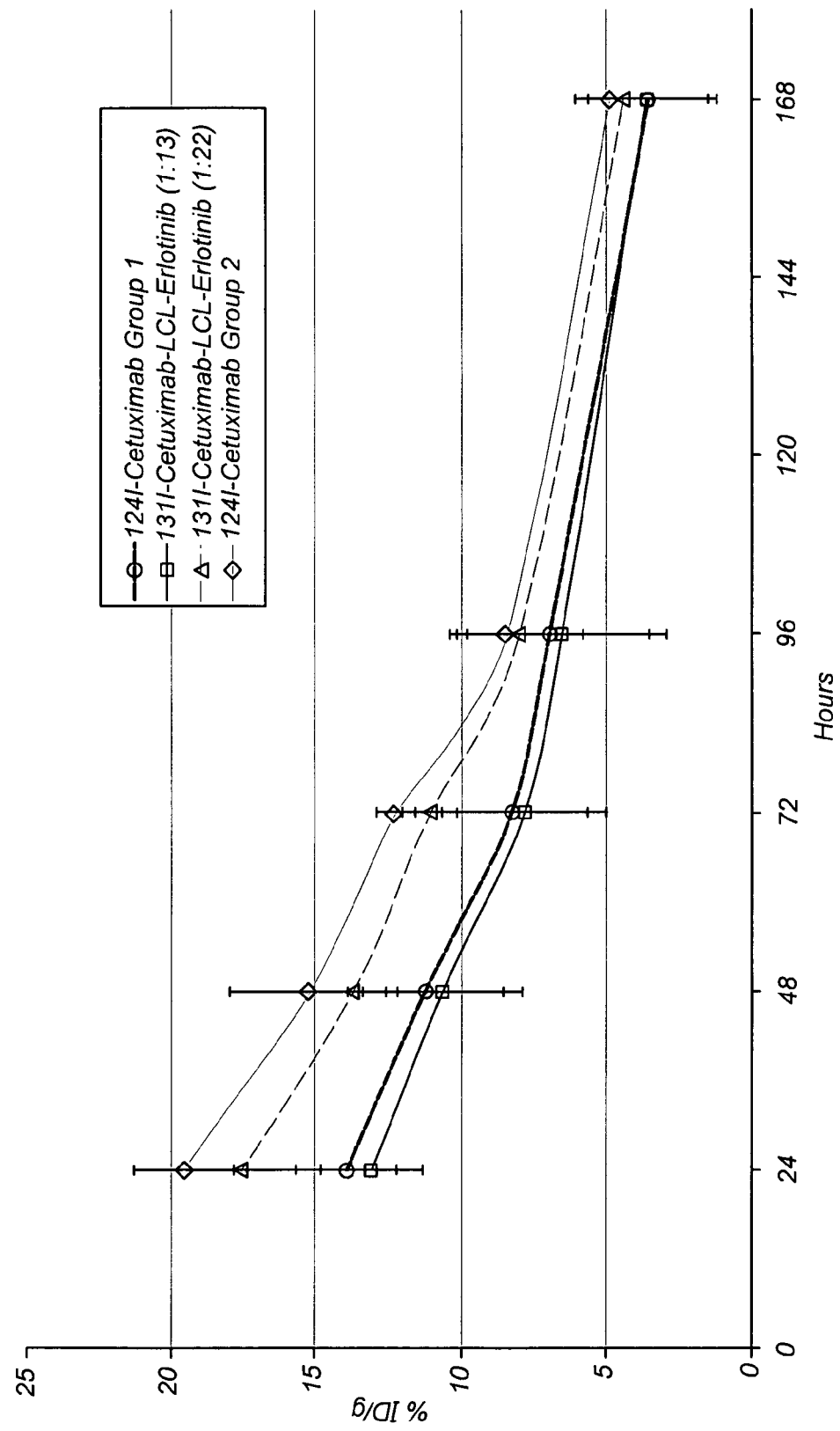
Fig. 3.3

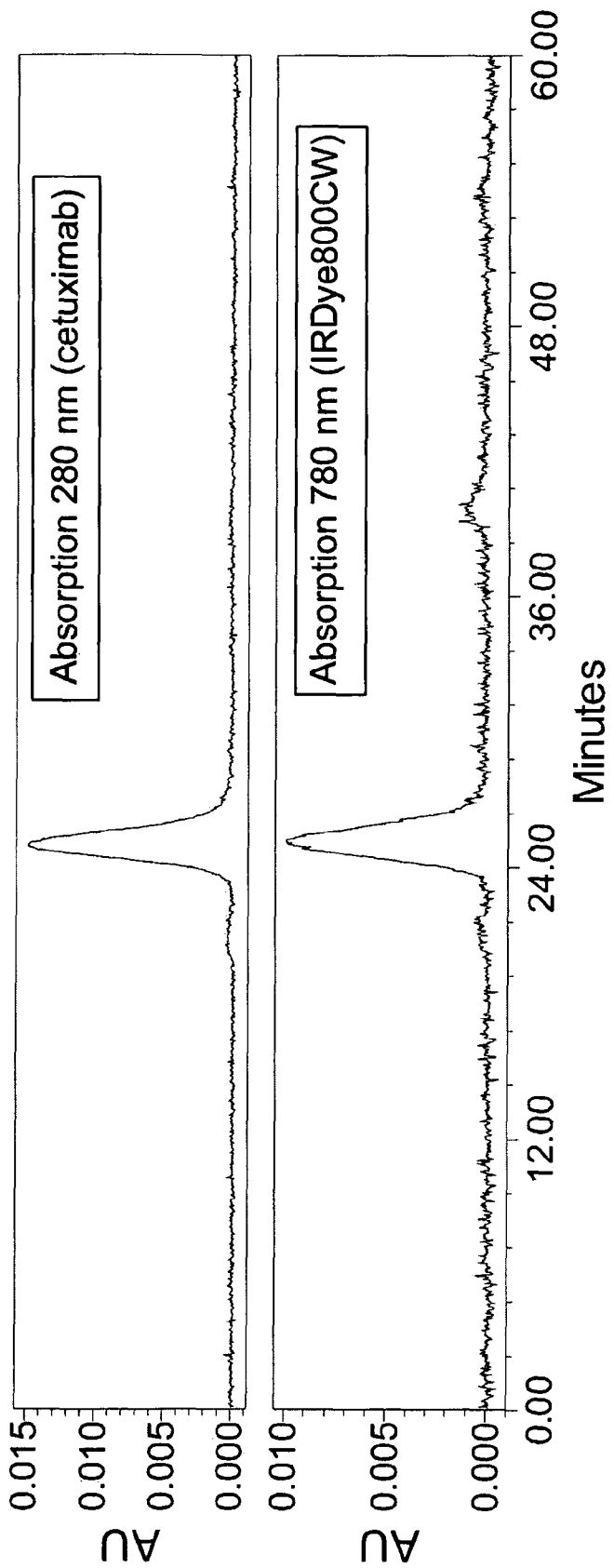
Fig. 4.1

Fig. 4.2
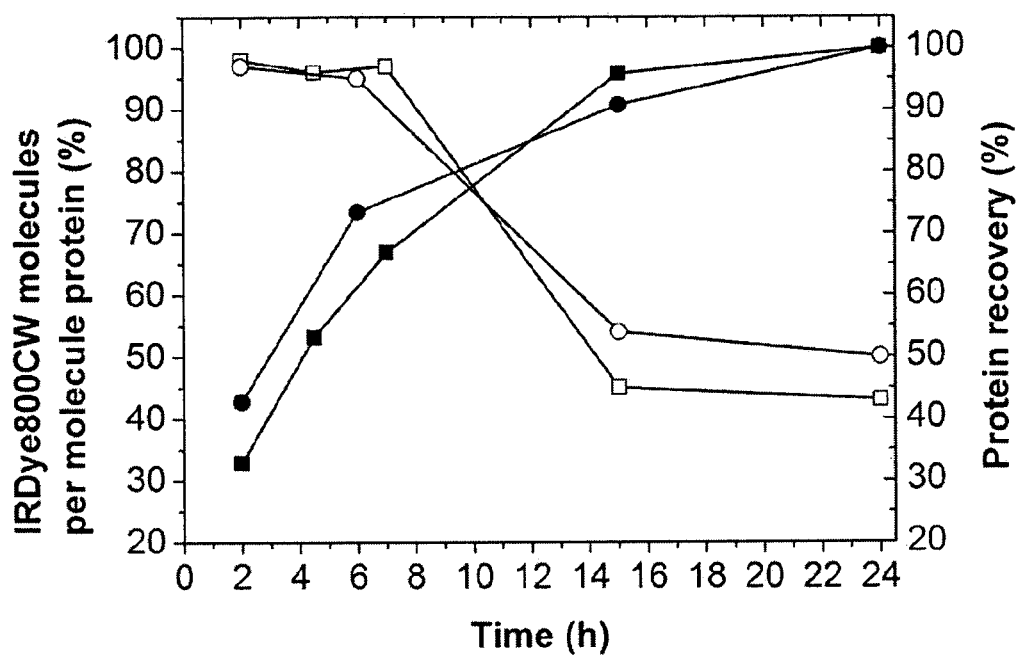
Fig. 5.1
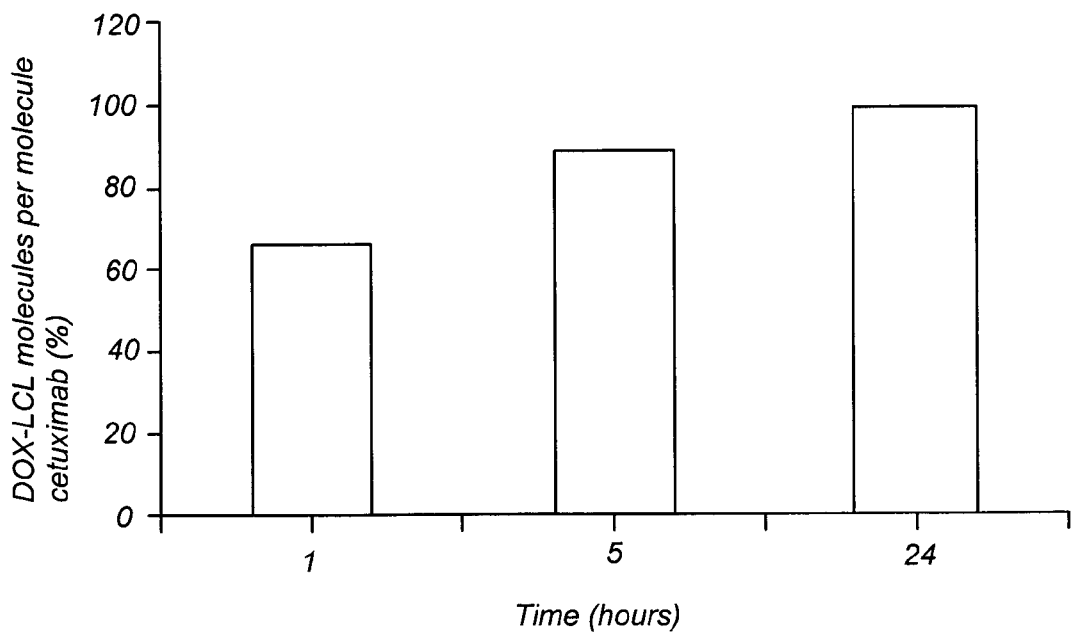

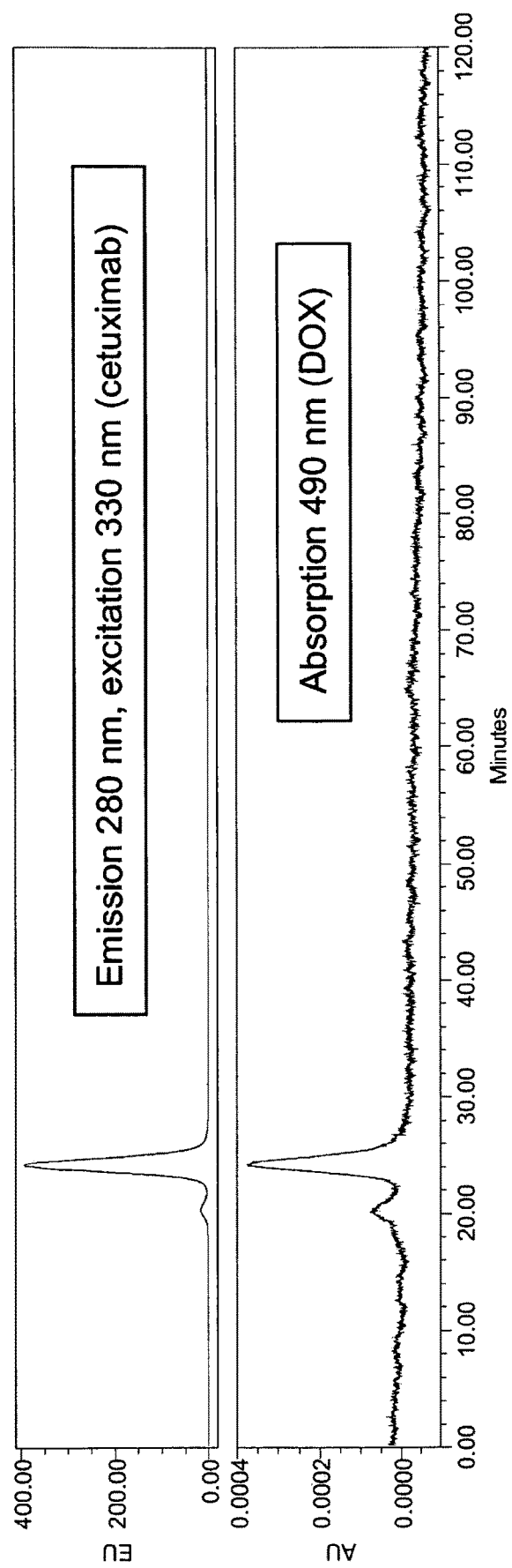
Fig. 5.2

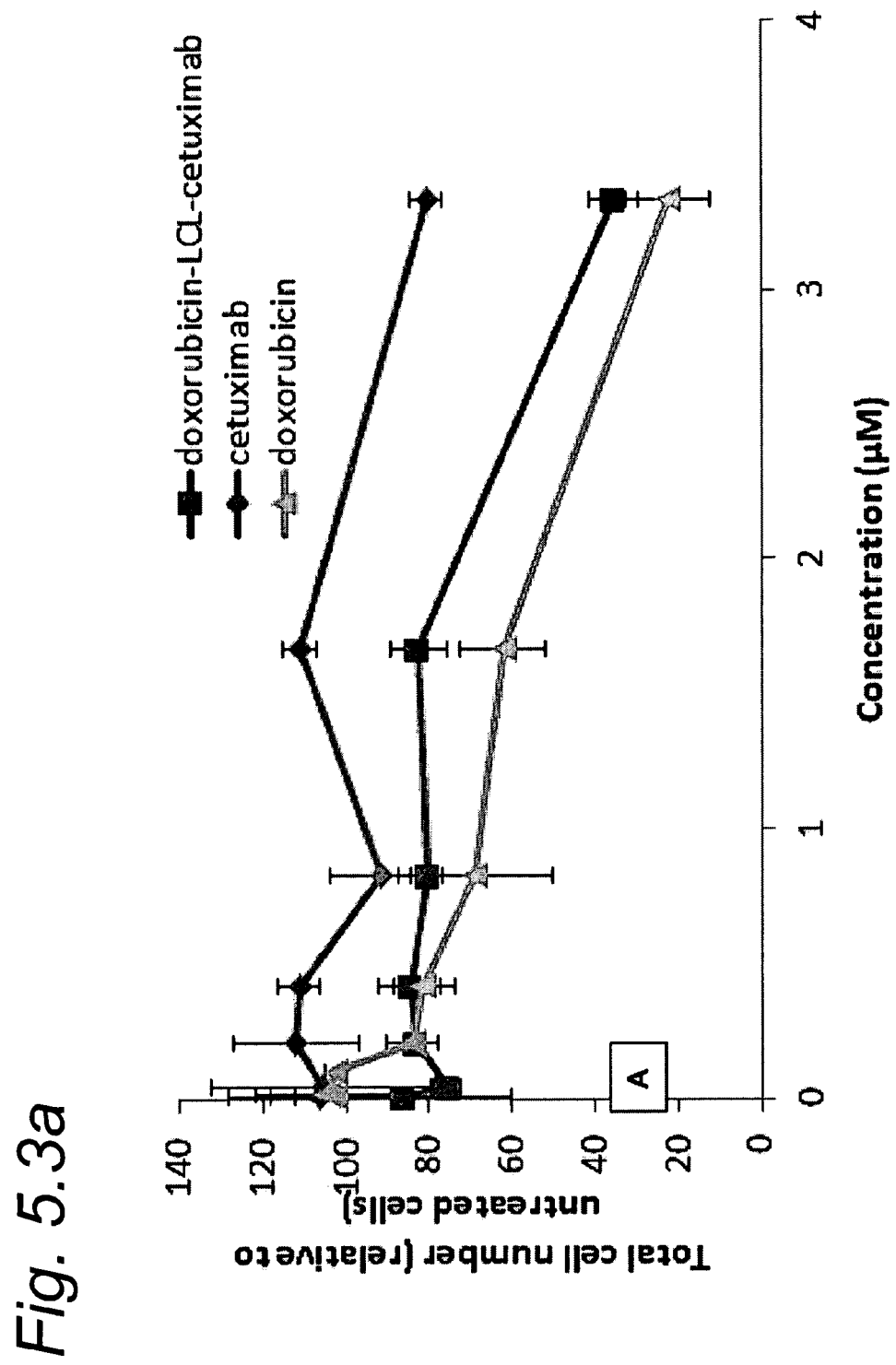
Fig. 5.3a

Fig. 5.3b
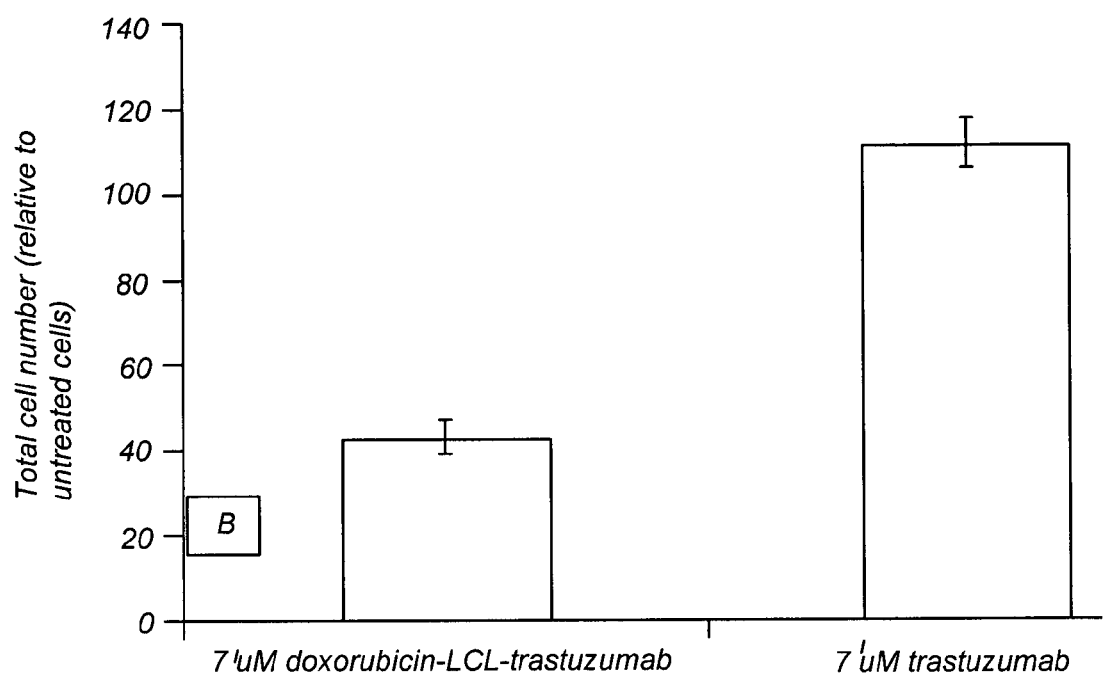

METHOD FOR PREPARING CELL TARGETING CONJUGATES, AND THE COMPLEXES OBTAINED

CROSS-REFERENCE TO RELATED APPLICATIONS

This application is a national phase entry under 35 U.S.C. § 371 of International Patent Application PCT/NL2013/050003, filed Jan. 4, 2013, designating the United States of America and published in English as International Patent Publication WO 2013/103301 A2 on Jul. 11, 2013, which claims the benefit under Article 8 of the Patent Cooperation Treaty to European Patent Application Serial No. 12150366.8, filed Jan. 6, 2012.

TECHNICAL FIELD

The disclosure relates generally to biotechnology and more particularly to a method for preparing cell-targeting conjugates by coupling at least one functional moiety, such as a therapeutic compound, diagnostic compound or chelating agent, to a targeting moiety. This disclosure also relates to the cell-targeting conjugates obtainable with this method and to pharmaceutical compositions comprising the cell-targeting conjugates.

BACKGROUND

Site-specific or targeted delivery of drugs is considered a valuable tool to improve the therapeutic efficacy and to reduce the toxicity of drugs. For example, antibody-drug-conjugates are known in the art, and consist of a recombinant antibody covalently bound to a small therapeutic compound (typically 300 to 1,000 Da) via a synthetic linker (S. C. Alley et al., *Curr. Opin. Chem. Biol.* 2010, 14:529-537).

Whereas non-targeted drug compounds or diagnostic compounds typically reach their intended target cells via whole-body distribution and passive diffusion or receptor-mediated uptake over the cell membrane, targeted drugs or targeted diagnostic compounds home-in and concentrate mainly at the targeted tissues. Consequently, targeted drugs (herein meant as drugs targeted by a targeting moiety) or diagnostic compounds require smaller dosages, while still allowing the drug to reach therapeutically or diagnostically effective levels inside or at the level of the target lesion or cells, thus improving the therapeutic or diagnostic window.

In this regard, it is important to note that, in general, it is favorable if the amounts of targeted therapeutic compounds that reach the target cells can be adjusted according to their efficacy; in other words, that the accumulation of therapeutic compounds at the target cell needs to be higher in case they are less potent (e.g., less cytotoxic). For diagnostic compounds, a high accumulation at the target cell is generally considered advantageous, unless this reduces the signal, such as, e.g., in the case of quenching.

The use of targeted diagnostic compounds is of great value for whole-body imaging and can be used for patient selection and response prediction for targeted therapeutics (personalized medicine) and for validation of therapeutic responses to targeted therapeutic compounds.

Furthermore, the preferred lipophilic or amphiphilic character of non-targeted drugs, which facilitates their easy passage over the cell membrane and which feature is not always in agreement with other requirements of the drug, is less relevant to targeted drugs. The targeting of therapeutic compounds or diagnostic compounds to specific cells is, therefore, a conceptually attractive method to enhance specificity, to decrease systemic toxicity and to allow for the therapeutic or in vivo diagnostic use of compounds that are, in principle, less suitable or unsuitable as systemic drugs. In general, drug delivery technologies are aimed at altering the interaction of the drug with the in vivo environment and achieve that objective by conjugation of the drug with other molecules, entrapment of the drug within matrices or particles, or simply by co-administration with other agents. The net result is either drug targeting or enhanced drug transport across biological barriers such that its bioavailability is improved with a reduction of the incidence of clinical side effects in subjects. Drug targeting is achieved when an alteration in the drug's biodistribution favors drug accumulation at the desired site, which site is usually remote from the administration site. Cell-selective delivery of therapeutic agents (drugs) can, in principle, be obtained by coupling drug molecules to targeting moieties, which targeting moieties are a member of a specific binding pair, i.e., a member from a pair of molecules, wherein one of the pair of molecules has an area on its surface or a cavity that specifically binds to, and is, therefore, defined as complementary with, a particular spatial and polar organization of the other molecule, so that the pair have the property of binding specifically to each other. Examples of types of specific binding pairs are antigen-antibody, biotin-avidin, hormone-hormone receptor, receptor-ligand, enzyme-substrate, and IgG-protein A. Particularly suitable targeting moieties from such binding pairs are macromolecular carriers, such as, for example, monoclonal antibodies, antibody fragments or engineered variants thereof, or low molecular weight carriers, such as, for example, peptides.

However, the linkage between the therapeutic compound and the targeting moieties often poses significant problems. For instance, the linking of lipophilic non-targeted therapeutic compounds to hydrophilic targeting moieties may be difficult, although methods are available in the prior art to achieve such linking. Furthermore, chemically reactive groups for conventional conjugation chemistry may be absent, or chemically reactive groups may be (abundantly) present, but (covalent) linkage may (irreversibly) inhibit the bioactivity of the coupled therapeutic compound.

As will be explained in more detail below, with the method of the disclosure, it is possible to prepare conjugates wherein the bioactivity of such compounds is substantially maintained or even improved, as may be observed by an increased half-life of such compounds.

In WO2007/011217, a method is described for linking therapeutic compounds to targeting moieties by using (transition) metal ion complexes. These metal ion complexes have a first reactive group for forming a coordination bond with a functional moiety, such as a therapeutic compound or a diagnostic compound (such as a tracer) or a chelating agent and a second reactive group for forming a coordination bond with a site of the targeting moiety. In WO2007/011217, it is stated that typical reaction conditions for formation of the coordination bond between the second reactive group of the metal ion complex and the targeting moiety are 37° C. for twenty-four hours. These conditions are not compatible with batch-size production of compounds for clinical use. First, the reaction conditions are relatively harsh, which has a negative effect on the binding affinity (such as, for instance, the immunoreactivity) of the targeting moiety and interferes with approval for clinical use. Further, the conditions used ask for extreme sterility precautions during production to prevent bacterial contamination and endotoxin formation. Furthermore, the conditions used constitute an endpoint reaction that does not provide for the choice of an optimal ratio of drug/targeting moieties, depending on the type of drug or tracer to be coupled.

These risks and issues may at least be partially taken care of by the methods according to this disclosure.

SUMMARY OF THE DISCLOSURE

The disclosure relates to a method for preparing a cell-targeting conjugate by coupling at least one functional moiety to a targeting moiety comprising the steps of:
i. providing functional metal ion constructs, which functional metal ion constructs comprise a metal ion complex with a first reactive group and a second reactive group, wherein the first reactive group of the metal ion complex has formed a coordination bond with a functional moiety;
ii. mixing the functional metal ion constructs with targeting moieties, such that the second reactive group of the metal ion complex of the functional metal ion constructs forms a coordination bond with the targeting moieties such that a conjugate is formed and wherein the immunoreactivity of the targeting moieties of the conjugate remains substantially the same as the immunoreactivity of the unbound targeting moieties; and
iii. separating the resulting conjugates from the mixture.

The disclosure described herein further relates to cell-targeting conjugates obtainable by such a method and to pharmaceutical compositions comprising such cell-targeting conjugates.

In a further aspect, this disclosure relates to these cell-targeting conjugates and pharmaceutical compositions thereof for use as a medicament or label, particularly for use in the treatment or diagnosis of cancer, inflammation, fibrosis, metabolic disorders, central nervous system diseases, liver cirrhosis, end-stage renal disease, infectious diseases or cardiovascular disorders.

Definitions

The term "functional metal ion construct" as used herein refers to a construct comprising a metal ion complex with a first reactive group and a second reactive group, wherein the first reactive group of the metal ion complex has formed a coordination bond with a functional moiety, such as a therapeutic compound or diagnostic compound. Hence, the first reactive group of the metal ion complex constitutes a binding site for the functional moiety.

The term "reactive group" of the metal ion complex refers to a chemical group, a free orbital reactive site or a ligand of the metal ion complex that is capable of forming a binding site for the relevant reactive groups of the targeting moiety and/or the functional moiety.

The term "functional" as used herein has its normal scientific meaning and refers to the situation wherein an item described as functional has a certain biological, chemical, therapeutical and/or diagnostic function.

The term "functional moiety" as used herein refers to a chemical group or molecule that has a certain biological, chemical, therapeutical and/or diagnostic function in or outside the body, such as the human body. Typical functional moieties are therapeutic compounds (i.e., drugs) or diagnostic compounds (i.e., tracers or dyes).

The term "targeting moiety" as used herein refers to a member of a specific binding pair, i.e., a member of a pair of molecules, wherein one of the pair of molecules has an area on its surface, or a cavity that specifically binds to, and is, therefore, defined as complementary with a particular spatial and polar organization of the other molecule, so that the pair have the property of binding specifically to each other. Examples of types of specific binding pairs are antigen-antibody, biotin-avidin, hormone-hormone receptor, receptor-ligand, enzyme-substrate, and IgG-protein A.

The term "separating" as used herein has its normal scientific meaning and refers to the separation of one species, such as a chemical compound from another species, such as a solvent. Within the context of the application, separating may be done at once or may be done in different steps, which steps may also be carried out at different locations.

The term "specific binding pair" as used herein has its normal scientific meaning and refers to a member from a pair of molecules, wherein one of the pair of molecules has an area on its surface or a cavity that specifically binds to, and is, therefore, defined as complementary with, a particular spatial and polar organization of the other molecule, so that the pair have the property of binding specifically to each other. Examples of types of specific binding pairs are antigen-antibody, biotin-avidin, hormone-hormone receptor, receptor-ligand, enzyme-substrate, and IgG-protein.

The term "targeted drug" as used herein refers to a drug coupled to a targeting moiety such as an antibody.

The term "immunoreactivity" as used herein has its normal scientific meaning and refers to the binding affinity of a member of a specific binding pair.

BRIEF DESCRIPTION OF THE DRAWINGS

FIG. 1.1 shows a binding plot of 131I-trastuzumab, 131I-trastuzumab-LCL-4-py-NBD (conjugation ratio 4:1) and 131I-trastuzumab-LCL-4-py-NBD (conjugation ratio 5:1) to HER2-expressing SKOV-3 cells as described in Example 1.

FIG. 1.2 shows a Lineweaver Burk plot (per Example 1) for binding of 13I-trastuzumab, $^{131}$I-trastuzumab-LCL-4-py-NBD (conjugation ratio 4:1) and $^{131}$I-trastuzumab-LCL-4-py-NBD (conjugation ratio 5:1) to HER2-expressing SKOV-3 cells.

FIG. 2.1 shows a binding plot (per Example 2) for binding of 89Zr-trastuzumab and 89Zr-trastuzumab-LCL-Rhodamine to HER2-expressing SKOV-3 cells.

FIG. 2.2 shows a Lineweaver Burk plot (per Example 2) for binding of 89Zr-trastuzumab and 89Zr-trastuzumab-LCL-Rhodamine to HER2-expressing SKOV-3 cells.

FIG. 3.1 shows binding plots of cetuximab and cetuximab-LCL-erlotinib with A431 cells as per Example 3.

FIG. 3.2 shows binding plots of trastuzumab and trastuzumab-LCL-erlotinib with SKOV-3 cells as per Example 3.

FIG. 3.3 shows blood kinetics of $^{124}$I-cetuximab and $^{131}$I-cetuximab-LCL-erlotinib in nude mice bearing A431 xenografts as per Example 3.

FIG. 4.1 shows GPC chromatograms of IRDye800CW-LCL-cetuximab as per Example 4.

FIG. 4.2 shows, after 6 hours, that 70% of IRDye800CW-LCL-chloride has coupled as compared to the amount that can be coupled after 24 hours as per Example 4.

FIG. 4.2 shows conjugation of IRDye800CW-LCL to mAb (closed symbols) and mAb recovery (open symbols) as a function of time (■ cetuximab ● trastuzumab) per Example 4.

FIG. 5.1 shows conjugation of DOX-LCL to cetuximab as a function of time as per Example 5.

FIG. 5.2 shows GPC chromatograms of DOX-LCL-cetuximab as per Example 5.

FIG. 5.3a and FIG. 5.3b show that DOX-LCL-antibody conjugates are more effective in killing cells than the unmodified antibodies.

DETAILED DESCRIPTION

The disclosure provides a method wherein the above-mentioned linkage problems of functional moieties are avoided and wherein the targeting moieties keep their targeting properties. In other words, by applying the method of the disclosure, the targeting moieties do not lose their immunoreactive ability (i.e., binding affinity) while being bound to one or more functional metal ion constructs.

A first aspect of this disclosure relates to a method for preparing a cell-targeting conjugate by coupling at least one functional moiety to a targeting moiety comprising the steps of:
  i. providing functional metal ion constructs, which functional metal ion constructs comprise a metal ion complex with a first reactive group and a second reactive group, wherein the first reactive group of the metal ion complex has formed a coordination bond with a functional moiety;
  ii. mixing the functional metal ion constructs with targeting moieties, such that the second reactive group of the metal ion complex of the functional metal ion constructs forms a coordination bond with the targeting moieties, such that a conjugate is formed and wherein the immunoreactivity of the targeting moieties of the conjugate remains substantially the same as the immunoreactivity of the unbound targeting moieties; and
  iii. separating the resulting conjugates from the mixture.

As said, by using the method of the disclosure, the immunoreactivity, i.e., binding affinity, of the targeting moieties of the conjugate according to the disclosure, remains substantially the same as the unbound targeting moieties, i.e., the targeting moieties before they were added to the reaction mixture. This is important because only when the immunoreactivity of the targeting moiety remains sufficiently high, it will be possible to deliver the conjugate comprising the functional moiety, such as a therapeutic compound or diagnostic compound, at the right place in the body. Moreover, although in the conjugates, according to the disclosure, the functional moiety is bound to a targeting moiety, the therapeutic or diagnostic availability of the therapeutic compound or diagnostic compound is maintained or even improved, as may be observed by an increased half-life and/or target site retention time of the therapeutic or diagnostic compound.

Another advantage of the disclosure is that it does not take very long to bind the targeting moiety to the second reactive group of the metal ion complex of the functional metal ion construct and that the reaction conditions for making this coupling are highly independent from the functional moiety bound to the first reactive group of the metal ion complex of the functional metal ion construct. By doing this, it is possible for users to quickly bind the desired functional metal ion construct to the suitable targeting moiety.

In the method according to the disclosure, the functional metal ion constructs are mixed with the targeting moieties under relatively mild conditions. In this regard, the term "mild conditions" means that the reaction conditions are chosen such that the immunoreactivity (i.e., binding affinity) of the targeting moieties stays substantially the same as the immunoreactivity of the unbound targeting moieties.

Within the context of the disclosure, the wording "substantially the same immunoreactivity as the unbound targeting moieties" means that the reaction conditions or the amount of functional metal ion constructs bound to the targeting moiety has not impaired the immunoreactivity, i.e., the binding affinity, of the targeting moiety. The immunoreactivity as referred to herein may be measured by a binding assay essentially as described in T. Lindmo, *J. Immunol. Methods,* 72:77-89, 1984. Furthermore, the immunoreactivity may also be determined by BIACORE analysis.

Preferably, the immunoreactivity of the targeting moiety has decreased not more than 10%, preferably not more than 5%, compared to the same targeting moiety that is not bound to a functional metal ion construct.

In this regard, it is noted that both the reaction conditions during the binding of the functional metal ion constructs and the targeting moieties, as well as the amount of functional metal ion constructs bound to a targeting moiety, influence the immunoreactivity (i.e., binding affinity) of the targeting moiety.

With respect to the reaction conditions, it is of importance that they are chosen such that the immunoreactivity of the targeting moieties is not substantially reduced. The most preferred reaction conditions for the targeting moieties are wherein the pH is around a physiological pH, i.e., about 8-9 at a temperature of about 37° C. and wherein the reaction time is as short as possible, such as 10 to 240 minutes. This means that if, for example, a higher reaction temperature is used, a lower reaction time should be used. The same applies to pH. If a higher or lower pH is used, the reaction time should be decreased in order to avoid loss of the immunoreactivity of the targeting moiety. Moreover, targeting moieties will precipitate at low or high pH when their isoelectric point is at low or high pH and, therefore, such conjugation conditions are not suitable.

The functional metal ion constructs are preferably mixed with the targeting moieties for 10 to 240 minutes, preferably 30 to 120 minutes, more preferably for 30 to 90 minutes, even more preferably for 45 to 90 minutes, and most preferably for about 60 minutes. This is a considerably shorter reaction time than has been used in the prior art, such as, for example, in WO2007/011217. Reaction times shorter than 30 minutes, such as lower than, e.g., 10 minutes, are less desirable as such rapid reactions run the risk of being non-homogeneous.

Due to the relatively short reaction time of the method of the disclosure, the biological properties of targeting moiety are not deteriorated and the targeting moiety keeps its original immunoreactivity and its original pharmacokinetic characteristics. Furthermore, due to the short reaction time, growth of unwanted bacteria in the reaction mixture is substantially avoided.

The mixing of the functional metal ion construct and the targeting moiety is preferably carried out at a temperature of 20° C. to 50° C., preferably 25° C. to 45° C., more preferably at 35° C. to 40° C., most preferably at about 37° C. Within this temperature range, the binding of the functional metal ion construct to the targeting moiety is optimal, without sacrificing the immunoreactivity of the targeting moiety. Especially in combination with the above-mentioned reaction times, excellent results are obtained.

In a preferred embodiment of the disclosure, the pH of the mixture of the functional metal ion construct and the targeting moiety is adjusted to pH 4-12, preferably to 6-10, most preferably about 7-9.

A suitable combination of reaction conditions is a temperature of 35° C. to 40° C., a pH of 8 to 9 and a reaction time of 30 to 100 minutes. Another suitable combination would be 30° C. to 35° C., a pH of 8-9 and a reaction time of 100 to 250 minutes. A further suitable combination would be 40° C. to 42° C., at a pH of 8-9 and a reaction time of 30 to 60 minutes.

As mentioned above, due to the mild reaction conditions used in the method according to the disclosure, the immunoreactivity of the targeting moiety is not substantially affected. This means that more functional metal ion constructs may be bound via coordination bonds to the targeting moiety without the latter losing its immunoreactivity.

However, a point may be reached wherein so many functional metal ion constructs have bound with a targeting moiety that it has lost its specific binding capabilities or pharmacokinetic properties. Hence, the amount of functional metal ion constructs bound to a targeting moiety should be chosen such that the immunoreactivity and/or pharmacokinetic properties are not lost.

Thus, conjugates of the disclosure may comprise one functional metal ion construct bound to one targeting moiety. However, since the immunoreactivity, i.e., binding affinity, of the targeting moiety is not substantially affected by the coupling reaction, more functional metal ion constructs may be bound to one targeting moiety. In this way, the window of application of the functional moieties, such as therapeutic window for therapeutic compounds or the diagnostic window for diagnostic compounds, is enlarged.

Preferably, at least two, even more preferably at least five, functional metal ion constructs are bound via coordination bonds with one targeting moiety.

It is particularly preferred that 1-30, preferably 2-20, more preferably 2-15 and most preferably 5-10 functional metal ion constructs are bound via coordination bonds with one targeting moiety. These ranges provide an optimal balance between drug efficacy, pharmacokinetics and binding affinity.

In the case where binding one or more functional metal ion constructs to one targeting moiety, it is preferred that the metal ion complex is a platinum complex.

Determining the amount of functional metal ion constructs bound to a targeting moiety can be done by the method described by Cohen et al., *EjNMMI Research* 2011, 1:31, although other methods may also be used. Preferably, the functional moieties of the functional metal ion constructs are therapeutic compounds.

The above-mentioned ratios of functional metal ion constructs to targeting moieties can be achieved by varying the ratios of the constituents in the reaction mixture. For example, if a ratio of ten functional metal ion constructs to one targeting moiety is used in the mixture, about five functional metal ion constructs will have formed a coordination bond with one targeting moiety. This is also referred to as the "coordination efficiency." Preferably, the coordination efficiency of binding the functional metal ion constructs to the targeting moiety is 10%-100%, more preferably 20%-100%, most preferably at least 40%.

After mixing during the above-mentioned time and at the above-mentioned temperatures, cell-targeting conjugates will have been formed. These conjugates are separated from the mixture by chromatography, preferably via size exclusion chromatography. It is particularly preferred to use so-called PD10 columns for separating the cell-targeting conjugates from the reaction mixture.

The targeting moieties used may be customized for the patient to be treated. In this regard, it is envisaged that patient-specific information may be used to identify the most suitable targeting moieties for that patient.

The reactive sites on the targeting moiety and the functional moiety are capable of forming coordination bonds with the (transition) metal ion complex. Within the context of the disclosure, the term "coordination bond" has its usual meaning, i.e., a covalent bond in which both electrons come from the same atom. Other terms used for a coordination bond is a "dipolar bond" or "dative covalent bond."

In a preferred embodiment, the metal ion complex is a platinum complex. The platinum complex may be a transplatinum complex or it may be a cis-platinum complex. The cis-platinum complex is preferred and preferably comprises an inert bidentate moiety as a stabilizing bridge. In another embodiment, the (platinum) metal ion complex comprises a tridentate moiety as a stabilizing bridge. In yet another embodiment, the metal ion complex comprises at least two (transition) metal ions, whether or not the same.

The second reactive group of the metal ion complex of the functional metal ion construct, i.e., the group that will form a coordination bond with the targeting moiety, may comprise a nitrate or chloride group before it is bound to the targeting moiety. During the binding reaction, the nitrate or chloride group leaves and the second reactive group of the functional metal ion construct will bind more easily to the targeting moiety, thereby forming the so-called "cell-targeting" conjugate. The use of such a nitrate group is even more preferred over a chloride group for reasons that it further increases the number of metal ion complexes that can be bound via coordination bonds with one targeting moiety.

In order to obtain a bond with adequate stability for in vivo applications, it is preferred that the targeting moiety and/or the functional moiety comprise one or more sulphur-containing reactive sites and/or one or more nitrogen-containing sites. It is particularly preferred that the functional moiety, such as a therapeutic compound, comprises one or more sulphur groups and/or one or more nitrogen groups, preferably aromatic nitrogen groups.

The functional moiety of the functional metal ion construct is, in a preferred embodiment of the disclosure, a therapeutic compound, such as a (super-)toxic drug or a kinase inhibitor, or a diagnostic compound, such as a fluorescent dye or a radioactive tracer ligated to a chelating agent.

It is particularly preferred when the functional moiety of the functional metal ion construct is a therapeutic compound that inhibits a signal transduction cascade in a cellular system, that it interferes with the cytoskeleton or intercalates in the DNA double helix. It is further preferred that the functional moiety has anti-inflammatory, anti-hypertensive, anti-fibrotic, anti-angiogenic, anti-tumor, immune-stimulating or apoptosis-inducing activity, and, preferably, the therapeutic compound has an anti-tumor activity.

In a preferred embodiment, the functional moiety of the functional metal ion construct is a therapeutic compound chosen from the group of kinase inhibitors, or pro-drugs thereof. In a particularly preferred embodiment of the disclosure, the kinase inhibitor is erlotinib, gefinitib, imatinib, pentoxifylline, PDTC, PTK1, SB202190, vatanalib, LY364947, Y27632, AG1295, or SP600125.

Alternatively, the functional moiety of the functional metal ion construct is an angiotensin receptor blocker, such as losartan.

Alternatively, the functional moiety of the functional metal ion construct is a recombinant protein, such as TNF-related apoptosis-inducing ligand (TRAIL). Alternatively, the functional moiety of the functional metal ion construct is a therapeutic radionuclide, such as the beta emitters 90Y or 177Lu, or the alpha emitter 211At.

Alternatively, the functional moiety of the functional metal ion construct is a (super-)toxic drug such as taxanes, anthracyclines, vinca alkaloids, calicheamicins, maytansinoids, auristatins and CC10065 analogs.

Besides using therapeutic compounds as the functional moiety, diagnostic compounds can also be used. In an alternative embodiment, the functional moiety of the functional metal ion construct is a fluorescent dye, such as IRDye800CW, DY-800, DY-831, ALEXA FLUOR®750 dye, ALEXA FLUOR® 790 dye, and indocyanine green.

Other diagnostic compounds, which may be used in the disclosure as functional moiety of the functional metal ion constructs, are radionuclides, PET-imageable agents, SPECT-imageable agents or MRI-imageable agents.

It is also possible to couple chelating agents as functional moiety to the first reactive group of the metal ion complex and, in a subsequent derivatization step, load these chelators with therapeutic or diagnostic radionuclides or non-radioactive metals. Possible chelating agents are EDTA, DPTA and desferioxamine. However, macrocyclic chelating agents may also be used, such as DOTA or p-SCN-Bn-DOTA, to which a transition metal PET radioisotope, a non-radioactive metal, or transition metal SPECT radioisotope, such as $^{99m}$Tc or $^{195m}$Pt is coupled.

Alternatively, more than one kind of functional moiety is used. In this way, it is possible to bind different functional moieties, e.g., different useful combinations of therapeutic compounds or different combinations of useful diagnostic compounds, to one targeting moiety. By doing this, a preferred combination of therapeutic compounds can be delivered to the tissue of interest.

The targeting moiety preferably comprises a member of a specific binding pair and is thus able to bind to distinctive parts of certain cells or tissues. In this way, the targeting moiety is able to bring the functional moiety, which is attached thereto via the metal ion complex, to the place of interest.

The targeting moiety may comprise antibodies, such as monoclonal antibodies, derivates, or fragments thereof, or may comprise peptides.

A "derivative of an antibody" is defined herein as an antibody that has been altered, such that at least one property, preferably an antigen-binding property, of the resulting compound is essentially the same in kind, not necessarily in amount. A derivative is provided in many ways, for instance, through conservative amino acid substitution, whereby an amino acid residue is substituted by another residue with generally similar properties (size, hydrophobicity, etc.), such that the overall functioning is likely not to be seriously affected.

A "fragment of an antibody" is defined as a part that has at least one same property as the antibody in kind, not necessarily in amount. The functional part is capable of binding the same antigen as the antibody, albeit not necessarily to the same extent. A fragment of an antibody preferably comprises a single domain antibody (also referred to as nanobody), a single chain antibody, a single chain variable fragment (scFv), a Fab fragment or a F(ab')2 fragment. Suitably, the targeting moiety is a monoclonal antibody, most preferably a monoclonal antibody chosen from the group of antibodies that have shown a capacity for selective tumor targeting, such as adalimumab, bevacizumab, catumaxomab, cetuximab, gemtuzumab, golimumab, infliximab, panitumumab, rituximab and trastuzumab, or combinations thereof.

Alternatively, the targeting moiety is an antibody fragment or engineered variant thereof, such as a therapeutic FAB, preferably ranibizumab, a diabody, a minibody, a domain antibody, an affibody, a nanobody, preferably ALX-0651, or an anticalcin.

As said, due to the mild reaction conditions and short duration of the binding reaction of the functional metal ion construct to the targeting moiety, the latter is in excellent condition and has retained most of its original (unbound) immunoreactivity. Even when loaded with more than one functional metal ion construct, the targeting moiety retains substantially its original unbound immunoreactivity, e.g., the reactivity of the targeting moiety as such.

A second aspect of the disclosure described herein relates to the cell-targeting conjugates obtainable by the above-mentioned method. The cell-targeting conjugates comprise a metal ion complex with a first reactive group and a second reactive group, wherein the first reactive group has formed a coordination bond with a functional moiety and the second reactive group has formed a coordination bond with a targeting moiety. The targeting moiety of such cell-targeting conjugates has substantially the same immunoreactivity (i.e., binding affinity) as the unbound targeting moieties as explained and defined above.

Since the immunoreactivity of the targeting moiety is not influenced substantially by the binding reaction of the functional metal ion constructs thereto, it is possible to load the targeting moiety with more than one functional metal ion construct.

Preferably, at least two, even more preferably at least five functional metal ion constructs are bound via coordination bonds with one targeting moiety.

It is particularly preferred that 1-30, preferably 2-20, more preferably 2-15 and most preferably 5-10 functional metal ion constructs are bound via coordination bonds with one targeting moiety.

In case of binding more than one functional metal ion construct to one targeting moiety, it is preferred that the metal ion complex is a platinum complex.

A third aspect of the disclosure relates to a pharmaceutical composition comprising a cell-targeting conjugate as described above, or obtainable by the method described above and a pharmaceutically acceptable carrier.

In accordance with the disclosure, the term "pharmaceutical composition" relates to compositions comprising the cell-targeting conjugates as described hereinabove. Such pharmaceutical compositions comprise a therapeutically effective amount of these cell-targeting conjugates and a pharmaceutically acceptable carrier.

These pharmaceutical compositions may be administered with a physiologically acceptable carrier to a patient, as described herein. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition, if desired, can also contain minor amounts of wetting or emulsifying agents, or pH-buffering agents.

These pharmaceutical compositions can take the form of solutions, suspensions, emulsions, tablets, pills, capsules, powders, sustained-release formulations, and the like. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, etc. Examples of suitable pharmaceutical carriers are described in "*Remington's Pharmaceutical Sciences*" by E. W. Martin. Such compositions will contain a therapeutically effective amount of the cell-targeting conjugates, preferably in purified form, together with a suitable amount of carrier so as to provide the form for proper administration to the patient. The formulation should suit the mode of administration.

In another preferred embodiment, the pharmaceutical composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water-free concentrate in a hermetically sealed container, such as an ampoule or sachet, indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Pharmaceutical grade organic or inorganic carriers and/or diluents suitable for oral and topical use can be used to make up compositions containing the therapeutically active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents. The compositions may also include one or more of the following: carrier proteins such as serum albumin, buffers, fillers such as microcrystalline cellulose, lactose, corn and other starches; binding agents; sweeteners and other flavoring agents; coloring agents; and polyethylene glycol. Additives are well known in the art, and are used in a variety of formulations.

A fourth aspect of the disclosure relates to the above-mentioned cell-targeting conjugates or the above-mentioned pharmaceutical compositions, for use in the treatment of cancer, inflammation, fibrosis, metabolic disorders, central nervous system diseases, liver cirrhosis, end-stage renal disease, infectious diseases or cardiovascular disorders.

A fifth aspect of the disclosure relates to a kit comprising functional moieties and targeting moieties according to this disclosure.

The applicants have found that a particular advantage of the use of a (transition) metal ion complex as a linker between a functional moiety, such as a therapeutic compound, and a targeting moiety in targeted drugs is that (transition) metal ion complexes provide for bonds that are strong enough to allow the deliverable compound to be transported to various tissues in vivo while remaining coupled to a targeting moiety. The reactivity of particularly platinum complexes toward a variety of reactive sites in drug molecules is a benefit in the application as a drug linking system, since it allows straightforward conjugation reactions under mild conditions that result in quantitative yields of the desired products. A further advantage of the use of (transition) metal ion complexes is that, depending on the functional moieties used, such complexes may support the coupling of a wide variety of biologically active compounds to targeting moieties, whereby the chemistry of the targeting moieties, as well as of the functional moieties (e.g., therapeutic compounds), can vary greatly.

The preparation of the functional metal ion constructs, such as a platinum(II) complex, for use in a method of this disclosure, can be prepared via any method known in the art. References can, for example, be found in Reedijk et al., *Structure and Bonding,* 67:53-89, 1987. The preparation of some trans-platinum complexes is disclosed in EP 0 870 770. Further preparation methods can be found in WO 96/35696 and WO 98/15564. Methods described in any of these publications are incorporated herein by reference.

The term "targeting moiety" as defined above refers to a member of a specific binding pair, i.e., a member of a pair of molecules wherein one of the pair of molecules has an area on its surface or a cavity that specifically binds to, and is, therefore, defined as complementary with, a particular spatial and polar organization of the other molecule, so that the pair have the property of binding specifically to each other. Examples of types of specific binding pairs are antigen-antibody, biotin-avidin, hormone-hormone receptor, receptor-ligand, enzyme-substrate, and IgG-protein A.

In a preferred embodiment, the targeting moiety comprises, as mentioned above, a compound or part of a molecule that functionally interacts with a binding site on the surface of the cell, also identified by the term "homing part." Thus, the targeting moiety through the presence of the homing part provides specificity for, or binding affinity for, one or more cell types.

Alternatively, the targeting moiety may consist of a homing part. In such an embodiment, for instance, an antibody, FAB, or nanobody as described above, is bonded directly to the functional metal ion construct. The molecule on the cell that is targeted by the targeting moiety can be any suitable target, such as, for instance, a cell surface receptor. Targeting moieties may include such homing parts as, but are not limited to, antibodies, antibody fragments, endogenous or non-endogenous ligands for a cell-surface receptor, antigen-binding proteins, viral surface components, proteins, for instance, those that bind viral surface components, growth factors, lectins, carbohydrates, fatty acids or other hydrophobic substituents, peptides and peptidomimetic molecules. Targeting moieties may either encompass complexes, wherein the homing part is complexed with macromolecules, to yield multivalent structures) or may comprise or consist of a small molecule in the form of an antibody fragment or a small protein or peptide, such as, for instance, lysozyme.

The term "functional moiety" as used herein refers, as defined above, to a compound that is carried or transported by the targeting moiety to the surface and/or interior of a cell. In aspects of the disclosure, the deliverable compound is a therapeutic or diagnostic compound.

The terms "functional moiety," as defined above, and "therapeutic compound" and "drug" are used interchangeably herein and represent any agent that can be applied for therapeutic or diagnostic use. Also, the therapeutic compound may be a prodrug, which requires (bio)chemical modification to reach its active form.

As said, the term "reactive group" of the metal ion complex refers to a chemical group, a free orbital reactive site or a ligand of the metal ion complex that is capable of forming a bond with reactive groups of the targeting moiety or the functional moiety. The term "(transition) metal ion complex," as used in the present application, refers to the linker system as described above, which is used to couple the targeting moiety to the functional moiety. A characteristic of such complexes is the presence therein of coordination bonds. Metal ions suitable for use in a (transition) metal ion complex used in this disclosure are metal ions capable of forming coordination bonds with ligands. Thus, transition metals such as Pt, Eu, Cu, Zn, Ni, Pd, Os and Cd are amenable for use in the disclosure. The (transition) metal ion complex of the disclosure consists of a central metal ion bound to a number of other molecules, namely, the targeting moiety and the functional moiety. The nature of the chemical bond formed between these moieties and metal can be thought of as involving the donation of a pair of electrons present on the functional moiety or targeting moiety or, in molecular orbital terms, as a molecular orbital formed by combining a filled orbital of the functional moiety or targeting moiety with a vacant orbital of the metal. Those atoms in the moieties that are directly involved in forming a chemical bond to the metal ion are, therefore, termed the "donor atoms," generally comprising elements of Groups V and VI of the periodic table, with nitrogen, and sulfur being those most preferred. Oxygen, phosphorus and arsenic can also be used.

The embodiments of this disclosure will now be illustrated by way of the following, non-limiting examples, in which a platinum complex platinum(II)ethylenediamine is used, either as Pt(en)Cl$_2$ or as Pt(en)(NO$_3$)$_2$, both being designated as LCL and also designated as Lx. Examples #1 and #2 comprise model experiments to illustrate the influence of reaction variables as mentioned in the description, whereas Examples #3 to #7 describe applications with targeting complexes of potential clinical relevance.

EXAMPLES

Example 1. Model Experiments with 4-py-NBD-LCL Targeting Complexes

Synthesis of 4-py-NBD-LCL-chloride

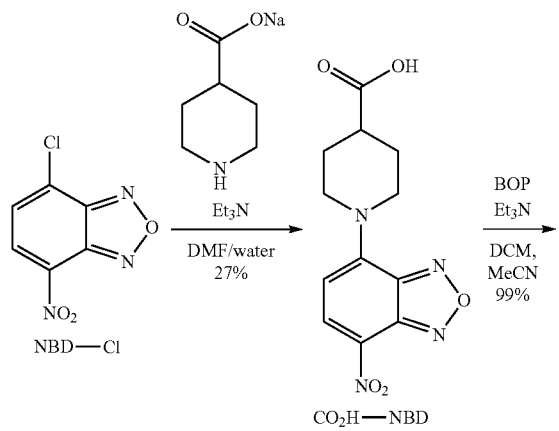

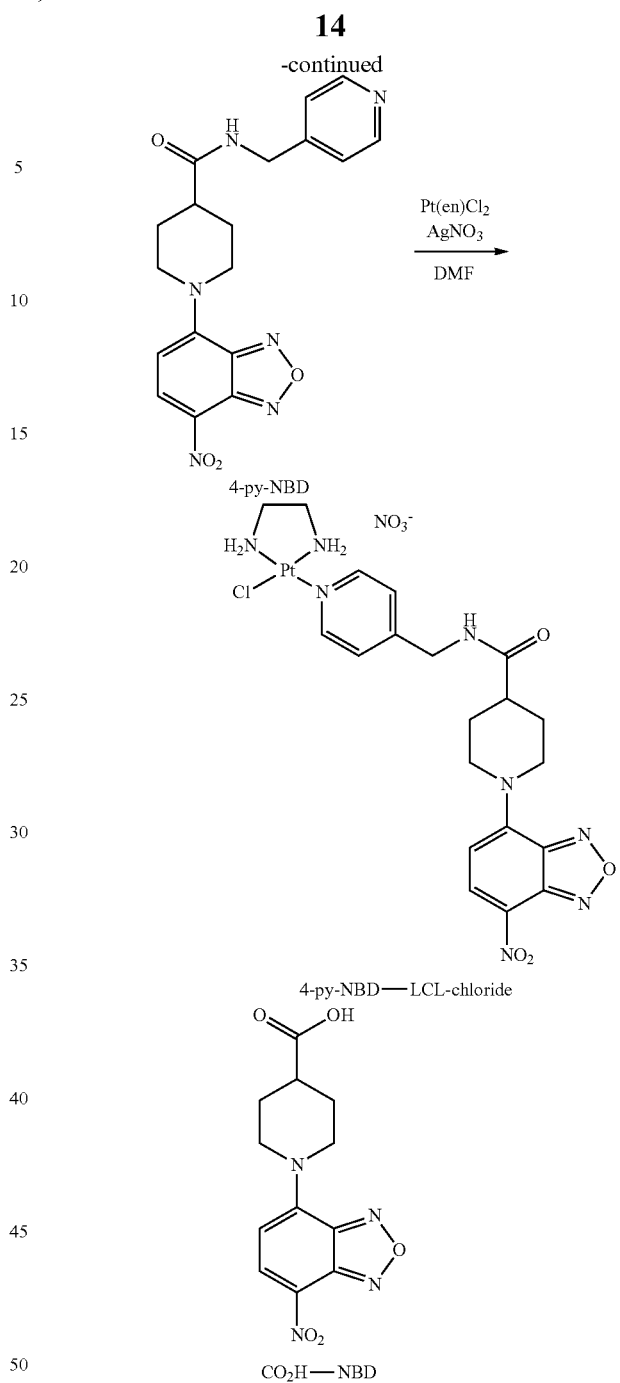

NBD-Cl (500 mg, 2.51 mmol) was dissolved in dimethylformamide (DMF 0.5 ml) and dropwise added to a solution of piperidine-4-carboxylic acid (971 mg, 7.52 mmol) in aqueous NaOH (1 M, 7.5 ml) at 0° C. After 5 minutes, the dark red reaction mixture was allowed to warm to RT. Another portion of piperidine-4-carboxylic acid (647 mg, 5.01 mmol) in NaOH (1 M, 5.0 ml) was added after 2 hours, and stirring was continued for 2.5 hours. The reaction mixture was poured into aqueous HCl (1 M, 100 ml) and the red precipitate was filtered off. The crude product was recrystallized from hot EtOH/MeOH to afford the product (199 mg, 27%) as red crystals. $^1$H-NMR (400 MHz DMSO-d6) ∂ 12.41 (br s, 1H), 8.45 (d, J=9.2 Hz, 1H), 6.66 (d, J=9.2 Hz, 1H), 4.66 (d, J=13.7 Hz, 2H), 3.67 (ddd, J=14.0, 11.2, 3.0 Hz, 2H), 2.76 (tt, J=10.3, 4.3 Hz, 1H), 2.11-2.03 (m, 2H) 1.76 (dtd, J=14.4, 10.9, 3.9 Hz, 2H). HRMS (ESI$^+$) C$_{12}$H$_{12}$N$_4$O$_3$Na [M+Na] calc 315.0700, found 315.0687.

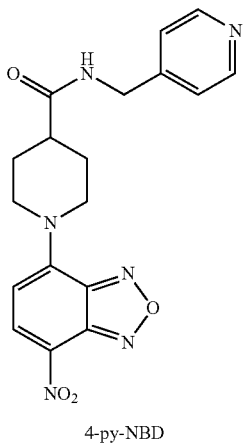 [SMILES: O=C(NCc1ccncc1)C1CCN(c2ccc([N+](=O)[O-])c3nonc23)CC1]

4-py-NBD

To a suspension of CO$_2$H-NBD (194 mg, 0.664 mmol) and triethylamine (235 mg, 2.32 mmol) in acetonitrile (ACN, 3 ml) at RT was added (Benzotriazol-1-yloxy)tris(dimethylamino) phosphonium hexafluorophosphate (BOP) (294 mg, 0.664 mmol). After 5 minutes, the suspension had largely cleared, at which point 4-(methylamine)pyridine (71.8 mg, 0.664 mmol) in dichloromethane (DCM, 6 ml) was added. After stirring for 15 minutes, an orange precipitate formed, which was stirred for 5 hours at RT. The reaction was diluted with DCM and washed with sat. aqueous NaHCO$_3$. The aqueous layer was extracted with DCM (3×) to dissolve all of the partially precipitated product, and the combined organic layers were washed with brine, dried with Na$_2$SO$_4$, filtered and evaporated onto silica gel. Purification by flash chromatography (1-5% MeOH in DCM) afforded the product (123 mg, 99%) as an orange-red solid. $^1$H-NMR (400 MHz, DMSO-d6) ∂ 8.55 (t, J=6.0 Hz, 1H), 8.50-8.45 (m, 3H), 7.24-7.20 (m, 2H), 6.68 (d, J=9.3 Hz, 1H), 4.79 (d, J=13.4 Hz, 2H), 4.30 (d, J=6.0 Hz, 2H), 3.66-3.56 (m, 2H), 2.75 (tt, J=11.0, 4.4 Hz, 1H), 2.07-1.98 (m, 2H), 1.87-1.75 (m, 2H). $^{13}$C-NMR (75 MHz, DMSO-d6) ∂ 173.7, 149.5, 148.6, 145.2, 144.9, 144.8, 136.4, 122.0, 120.6, 103.4, 49.4, 41.0, 40.7, 28.5. HRMS (ESI$^+$) C$_{18}$H$_{19}$N$_6$O$_4$ [M+H] calc 383.1462, found 383.1490. HRMS (ESI$^+$) C$_{13}$H$_{19}$N$_6$O$_4$ [M+H] calc 383.1462, found 383.1490.

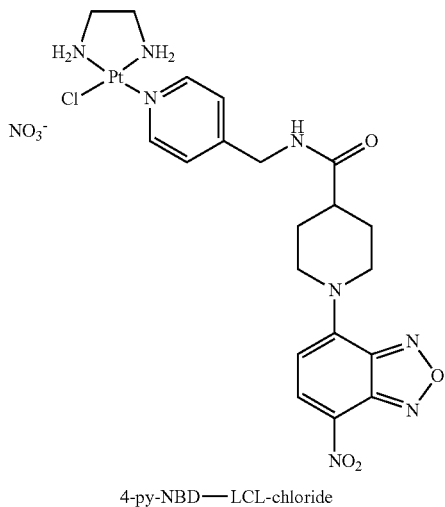

4-py-NBD—LCL-chloride

Silver nitrate (26.0 mg, 0.153 mmol) was added to a suspension of Dichloro(ethylenediamine)platinum(II) (Pt(en)Cl2, 50 mg, 0.153 mmol) in DMF and the reaction was protected from light and stirred for 24 hours. The grey suspension was filtered over Celite and washed with DMF (1 ml). 4-py-NBD (46.9 mg, 0.123 mmol) was added, resulting in a suspension, which cleared within 15 minutes. After 24 hours, the solvent was evaporated and the residue was suspended in 2.5% MeOH in DCM (30 ml) and stirred for 1 hour. The suspension was filtered and the orange solid was then partially dissolved in MeOH (20 ml) at RT and filtered. The filtrate was concentrated to about 5 ml and ether was dropwise added under stirring to precipitate the product. Finally, filtration of the suspension afforded the product (23.0 mg, 26%) as an orange-red solid. A portion of this material was further purified by semi-preparative HPLC (Alltima C18 column, 5 m, 250×10 mm, Eluent A: 100 mM triethylammonium acetate (TEAA) buffer, pH=5.0/ACN (9:1, v:v), Eluent B: 100 mM TEAA buffer, pH=5.0/ACN (3:7, v:v), isocratic elution with 4:1 A:B, flow 4 ml/minute, retention time product: 19.1 minutes). The product was collected at 0° C. and, after elution, the fractions containing product were combined, frozen and lyophilized. Traces of buffer were removed by redissolving the product in MILLI-Q® water (3 ml), followed by lyophilization to give the product (10 mg, 59%) as an orange-red solid. $^{195}$Pt-NMR (DMF-d6): δ −2506 ppm. HPLC (85%).

Coupling of 4-py-NBD-LCL-chloride to Cell-Targeting Moieties

Trastuzumab-LCL-4-py-NBD; Conjugation Ratio 4:1

4-py-NBD-LCL-chloride (0.240 ml, 5 mM in 20 mM NaCl(aq), 20 equiv.) was added to a solution of the anti-HER2 antibody trastuzumab (0.426 ml, 21 mg/ml) and tricine/NO3-buffer (24 μl, 0.25 M tricine, 1 M NaNO3, pH=8.5), final volume 690 ml. The mixture was placed in a THERMOMIXER® at 37° C. for 2 hours, after which the conjugation mixture was charged on a prewashed PD-10 column and eluted with tricine/NO$_3$-buffer. The conjugation ratio and recovery were determined by comparison of the UV-absorption at 280 nm and 472 nm of the protein fractions using a calibration curve of both trastuzumab and 4-py-NBD-LCL-chloride in tricine/NaNO$_3$-buffer. The average ratio of LCL-NBD:antibody was 3.9 with a recovery of 95%.

Trastuzumab-LCL-4-py-NBD; Conjugation Ratio 5:1

4-py-NBD-LCL-chloride (0.240 ml, 5 mM in 20 mM NaCl(aq), 20 equiv.) was added to a solution of trastuzumab (0.426 ml, 21 mg/ml), tricine/NO$_3$-buffer (36 μl, 250 mM tricine, 1 M NaNO3, pH=8.5) and MILLI-Q® (0.324 ml), final volume 1.03 ml). The mixture was placed in a THERMOMIXER® at 37° C. for 4 hours, after which the conjugation mixture was charged on a prewashed PD-10 column and eluted with tricine/NO$_3$-buffer. The conjugation ratio and recovery were determined by comparison of the UV-absorption at 280 nm and 472 nm of the protein fractions using a calibration curve of both trastuzumab and 4-py-NBD-LCL-chloride in tricine/NaNO$_3$-buffer. The average ratio of LCL-NBD:antibody was 5:1 with a recovery of 95%.

Radiolabeling of Trastuzumab and
trastuzumab-LCL-4-py-NBD $^{131}$I-trastuzumab

According to the general IODO-GEN-based procedure for radiolabeling of trastuzumab with $^{131}$I (Tijink et al., *Eur. J. Nucl. Med. Mol. Imaging* 36:1235-1244, 2009; see also Example 3), labeling of trastuzumab-LCL-4-py-NBD (504 μg) with 11.3 MBq $^{131}$I with a reaction time of 1 minute afforded $^{131}$I-trastuzumab-LCL-4-py-NBD (3.2 MBq, 28% overall yield). Radiochemical purity: TLC (92.7%), HPLC (100%), SDS-Page (>90%).

$^{131}$I-trastuzumab-LCL-4-py-NBD; Conjugation Ratio 4:1

According to the general IODO-GEN-based procedure for radiolabeling of trastuzumab with $^{131}$I (Tijink et al., *Eur. J. Nucl. Med. Mol. Imaging* 36:1235-1244, 2009) labeling of trastuzumab-LCL-4-py-NBD (498 μg) with 8.6 MBq $^{131}$I with a reaction time of 1 minute afforded $^{131}$I-trastuzumab-LCL-4-py-NBD (1.5 MBq, 18% overall yield). Radiochemical purity: TLC (97.4%), HPLC (100%), SDS-Page (>90%).

$^{131}$I-trastuzumab-LCL-4-py-NBD; Conjugation Ratio 5:1

According to the general IODO-GEN-based procedure for radiolabeling of trastuzumab with $^{131}$I (Tijink et al., *Eur. J. Nucl. Med. Mol. Imaging* 36:1235-1244, 2009) labeling of trastuzumab-LCL-4-py-NBD (396 μg) with 13.1 MBq $^{131}$I with a reaction time of 1 minute afforded $^{131}$I-trastuzumab-LCL-4-py-NBD (4.5 MBq, 35% overall yield). Radiochemical purity: TLC (99.2%), HPLC (99.7%), SDS-Page (>90%).

Immunoreactivity of
$^{131}$I-trastuzumab-LCL-4-py-NBD Conjugates and
$^{131}$I-Trastuzumab The immunoreactivity of monoclonal antibodies as targeting moieties can be assessed with a binding assay. This binding assay was first described by Lindmo et al. (*J. Immunol. Methods*, 1984) and consists of a serial dilution of target cells. Radiolabeled 4-py-NBD-LCL cell-targeting complexes were added to this dilution and after an overnight incubation at 4° C., the cells were spun down and radioactivity in both the pellet and supernatant were measured in a gamma-counter and the percentage of bound and free radioactivity (representing the fractional binding of the cell-targeting complex) can be calculated. The immunoreactivity of anti-HER2 $^{131}$I-trastuzumab-LCL-4-py-NBD conjugates was determined using 2% paraformaldehyde fixed HER2-expressing SKOV-3 cells and compared to $^{131}$I-trastuzumab. Five serial dilutions (ranging from 5×10$^6$ cells/tube to 3.1×10$^5$ cells/tube) were prepared with 1% BSA in PBS. Excess of unlabeled trastuzumab was added to a second tube with the lowest concentration of cells to determine nonspecific binding. Radiolabeled antibody was added to each tube, and samples were incubated overnight at 4° C. Cells were spun down, radioactivity in the pellet and supernatant was measured in a gamma-counter and the percentage of bound and free radioactivity was calculated. Data were graphically analyzed in a modified Lineweaver Burk plot and the immunoreactivity at the highest cell concentration was taken for comparison. As shown in FIG. 1.1 and FIG. 1.2, no decrease in immunoreactivity was observed for trastuzumab-LCL-4-py-NBD conjugation ratio 4:1 (immunoreactive fraction 95.7%) and trastuzumab-LCL-4-py-NBD conjugation ratio 5:1 (immunoreactive fraction 97.1%) as compared to $^{131}$I-trastuzumab (immunoreactive fraction 96.7%).

FIG. 1.1 shows a binding plot of 131I-trastuzumab, 131I-trastuzumab-LCL-4-py-NBD (conjugation ratio 4:1) and 131I-trastuzumab-LCL-4-py-NBD (conjugation ratio 5:1) to HER2-expressing SKOV-3 cells.

FIG. 1.2 shows a Lineweaver Burk plot for binding of $^{131}$I-trastuzumab, $^{131}$I-trastuzumab-LCL-4-py-NBD (conjugation ratio 4:1) and $^{131}$I-trastuzumab-LCL-4-py-NBD (conjugation ratio 5:1) to HER2-expressing SKOV-3 cells. Note that binding of anti-HER2 antibody trastuzumab to HER2-expressing SKOV-3 cells has not been affected by coupling of up to 5 LCL-4-py-NBD groups per mAb molecule.

Example 2. Model Experiments with rhodamine-LCl Targeting Complexes

Synthesis of Rhodamine-LCl-chloride

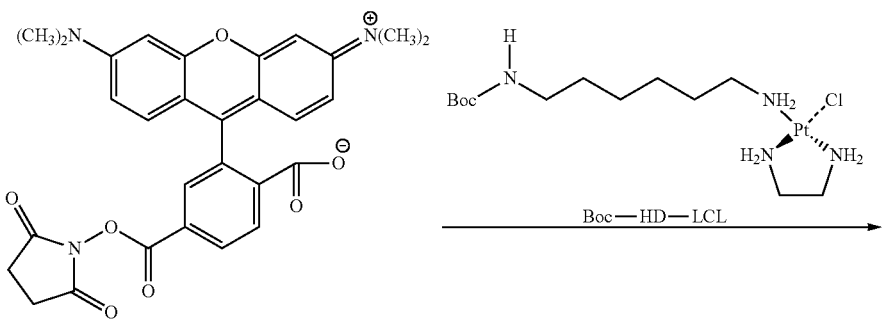

-continued

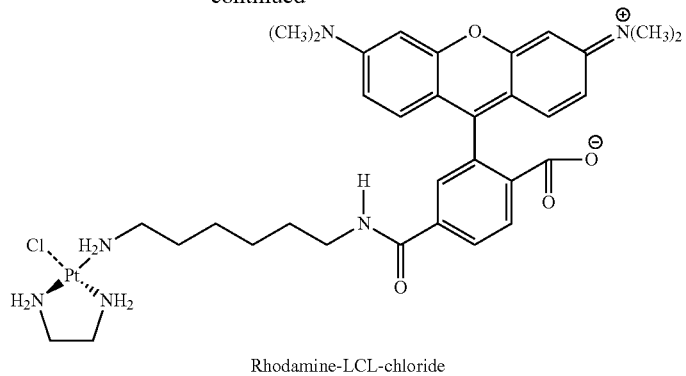

Rhodamine-LCL-chloride

Dichloro(ethylenediamine)platinum(II) (Pt(en)Cl2; 300 mg, 1.76 mmol, dissolved dimethylformamide (DMF; 30 ml)) was converted into Pt(en(NO3)Cl (LCL-chloride) by adding 1 molar equivalent of AgNO3 (520 mg, 1.76 mmol, dissolved in 52 ml of DMF) divided into four equal portions. Each addition was separated by 2 hours and the mixture was stirred in the absence of light, at ambient temperature. The grey precipitated silver chloride was removed by filtration over a 0.2 µm membrane filter 16 hours after the last addition. The resulting pale yellow solution was stored at 4° C. The identity and purity of the product was confirmed by $^{195}$Pt-NMR (DMF-d6): ∂Pt −2075 ppm.

N-tert-Butoxycarbonyl-1,6-hexanediamine (315 mg, 1.5 mmol) (Boc-HD) was dissolved in xylene (25 ml) and reacted with LCL-chloride (641 mg, 1.8 mmol) at 40° C. for 16 hours. Subsequently, the solvents were removed in vacuo and the remaining product was redissolved in a minute amount of MILLI-Q® water and stored overnight at 4° C. Insoluble yellow particles of residual [Pt(en)Cl(NO3)] were removed by filtration through membrane filters (1.0 µm). The clear filtrate was lyophilized affording a white fluffy powder (yield 74%). 1H-NMR (300 MHz, D20) ∂=3.11 (2H), 2.71 (4H), 2.63 (2H), 1.69 (2H), 1.52 (2H), 1.46 (9H), 1.39 (4H) ppm; $^{195}$Pt-NMR: ∂=2625 ppm.

Boc-HD-LCL (28 mg, 0.05 mmol) was dissolved in HCl (2 ml, 200 mM) and stirred overnight at 50° C. The pH of the solution was increased to 8.0 by adding small quantities of 1 M NaOH. This solution was then mixed 6-carboxyte-tramethylrhodamine-SE NHS ester (21 mg, 0.04 mmol) dissolved in 2.1 ml DMF. The mixture was allowed to react for 16 hours at room temperature. Solvents were removed in vacuo and the remaining product was redissolved in the minimal amount of loading buffer and subsequently purified by semi-preparative HPLC (SOURCE™ 15 RPC column, Eluent A: 95% NaCl (20 mM)/5% isopropanol; Eluent B: 10% NaCl (20 mM)/90% isopropanol; gradient elution (0% B from 0-5.78 minutes; 0-40% B from 5.78-34.7 minutes; 40-100% B from 34.7-37.6 minutes; 100% B from 37.6-46.3 minutes; 100.0% B from 46.3-49.2 minutes; 0% B from 46.3-57.9 minutes), flow 4.0 ml/minute). Elution buffers were subsequently removed by co-evaporation in vacuo (yield 22%). The identity and purity of the final product Rhodamine-LCL-chloride was confirmed by HPLC (>90%) and $^{195}$Pt-NMR (DMF-d6): −2543 ppm.

Optimization of Conjugation Conditions for trastuzumab-LCL-Rhodamine

The conjugation of Rhodamine-LCL-chloride with trastuzumab was used as a model system for the optimization of reaction conditions for conjugation of LCL-chloride complexes to cellular targeting complexes.

Buffer and pH

The effect of buffer and pH on the conjugation ratio was investigated by reaction of Rhodamine-LCL-chloride with trastuzumab in different buffers at pH=5.5-8.5. 4-Morpholineethanesulfonic acid (MES) and 4-(2-Hydroxyethyl)piperazine-1-ethanesulfonic acid (HEPES) were selected as potentially suitable alternatives to tricine as these buffers have a low affinity for metals (Good et al., Biochemistry 1966, 467-477) and their pH range allows for exploration of acidic to basic pH.

TABLE 2.1

Effect of buffer and pH on conjugation ratio for the conjugation of trastuzumab with Rhodamine-LCL-chloride.

| Entry[a] | Buffer | pH | Conjugation ratio (LCL:mAb) |
|---|---|---|---|
| 1 | MES | 5.5 | 0.8 |
| 2 | MES | 6.7 | 1.8 |
| 3 | HEPES | 6.8 | 1.8 |
| 4 | HEPES | 8.2 | 3.0 |
| 5[b] | tricine | 8.5 | 3.2 |

[a] Conditions: 37° C., 24 hours, final conc. trastuzumab; 2.5 mg/ml, buffer (2.5 mM), NaNO3 (10 mM), Rhodamine-LCL-chloride (20 equiv).
[b] tricine (2.5 mM) and NaNO3 (100 mM).

As shown in Table 2.1, a strong pH-effect was observed with the highest conjugation ratios of 3.0-3.2 obtained at pH=8.0-8.2 (Entry 4 and 5). No effect of the buffer on the conjugation ratio could be observed (Entry 2-3). Likewise, carrying out the reaction with tricine as the buffer at pH=8.5 (Entry 5) resulted in only a minor improvement when compared to the results obtained with HEPES at similar pH (Entry 5).

Concentration Tricine/NO3 Buffer

To investigate the effect of the buffer concentration on the conjugation ratio, Rhodamine-LCL-chloride was reacted with trastuzumab at various buffer concentrations ranging from 0-87% tricine (250 mM)/NO3 (1 M) buffer.

TABLE 2.2

Effect of buffer concentration on conjugation ratio for the conjugation of trastuzumab with Rhodamine-LCL-chloride.

| Entry[a] | Tricine/NO3[b] (%) | Conjugation ratio (LCL:mAb) |
|---|---|---|
| 1 | 0 | 0.2 |
| 2 | 5 | 1.0 |
| 3 | 10 | 1.6 |
| 4 | 25 | 0.6 |
| 5 | 50 | 0.4 |
| 6 | 75 | 0.4 |
| 7 | 87 | 0.3 |

[a]Conditions: 37° C., 24 hours, final conc. Trastuzumab; 2.5 mg/ml, 10 equiv of Rhodamine-LCL-chloride.
[b]Tricine (250 mM), NaNO$_3$ (1M).

The highest conjugation ratio of 1.6 was obtained with 10% tricine (250 mM)/NaNO$_3$ (1 M) (Entry 3).

Ratio mAb:LCL

To determine the optimal mAb:LCL ratio for the conjugation of Rhodamine-LCL-chloride with trastuzumab, the latter was reacted with excess Rhodamine-LCL-chloride with ratios varying from 1:5-1:50 trastuzumab:Rhodamine-LCL-chloride (mAb:LCL). (Table 2.3) Under the experimental conditions, the highest conjugation ratio of 3.8 was obtained at a mAb:LCl ratio of 1:20 (Entry 3). Increasing the ratio to 1:50 (Entry 4) resulted in precipitation of the protein, which prevented reliable determination of the average conjugation ratio.

TABLE 2.3

Effect of mAb:LCL ratio on conjugation ratio for the conjugation of trastuzumab with Rhodamine-LCL-chloride.

| Entry[a] | mAb:LCL ratio | Conjugation ratio (LCL:mAb) |
|---|---|---|
| 1 | 1:5 | 1.6 |
| 2 | 1:10 | 2.3 |
| 3 | 1:20 | 3.8 |
| 4 | 1:50 | 2.7[b] |

[a]Conditions: 37° C., 24 hours, final conc. trastuzumab; 2.5 mg/ml, tricine (25 mM) and NaNO3 (100 mM), pH = 8.5.
[b]Precipitation occurred. Conjugation ratio refers to conjugate still in solution.

Reaction Time

To explore the kinetics of the conjugation reaction, the reaction of Rhodamine-LCL-chloride (10 equiv) with trastuzumab was run for 1, 2, 6 and 24 hours under otherwise identical conditions. (Table 2.4) As expected, a steady increase in conjugation rate was observed, resulting in a maximum conjugation ratio of 2.3 after 24 hours (Entry 4).

TABLE 2.4

Effect of reaction time on conjugation ratio for the conjugation of trastuzumab with Rhodamine-LCL-chloride.

| Entry[a] | Reaction time (hours) | Conjugation ratio (LCL:mAb) |
|---|---|---|
| 1 | 1 | 0.4 |
| 2 | 2 | 0.7 |
| 3 | 6 | 1.3 |
| 4 | 24 | 2.3 |

[a]Conditions: 37° C., final conc. trastuzumab; 2.1 mg/ml, 10 equiv of Rhodamine-LCL-chloride tricine (25 mM) and NaNO3 (100 mM), pH = 8.5.

The reaction with Rhodamine-LCL-chloride could be significantly accelerated when the reaction was conducted at higher concentration and with 20 equiv of Rhodamine-LCL-chloride. (Table 2.5)

Under these conditions, a conjugation ratio of 2.5 was achieved after 6 hours (Entry 3).

TABLE 2.5

Increase in reaction rate when using 20 equiv of Rhodamine-LCL-chloride under more concentrated reaction conditions in the conjugation reaction with trastuzumab.

| Entry[a] | Reaction time (hours) | Conjugation ratio (LCL:mAb) |
|---|---|---|
| 1 | 2 | 1.3 |
| 2 | 4 | 1.8 |
| 3 | 6 | 2.5 |

[a]Conditions: 37° C., final conc. trastuzumab; 8.3 mg/ml, 20 equiv of Rhodamine-LCL-chloride tricine (83.8 mM) and NaNO3 (335 mM), pH = 8.5

89Zr-Labeling of Trastuzumab and trastuzumab-LCL-rhodamine

89Zr-trastuzumab

N-sucDf-trastuzumab (500 µg) was radiolabeled with 13.9 MBq 89Zr using published procedures (Verel et al., *Journal of Nuclear Medicine* 2003, 1271-1281) to afford 89Zr-trastuzumab (10.4 MBq, 77% overall yield). Radiochemical purity: TLC (96%), HPLC (95%), SDS-Page (>90%).

89Zr-trastuzumab-LCL-Rhodamine

N-sucDf-trastuzumab (0.300 ml, 5 mg/ml) was reacted with Rhodamine-LCL-Cl (0.020 ml, 5 mM), tricine/NO3-buffer (60 µl, 250 mM tricine, 1 M NaNO3, pH=8.5) and MILLI-Q® (0.220 ml, final volume 0.6 ml) for 24 hours in a Thermoshaker at 37° C. A portion of the conjugation mixture (0.5 ml) was charged on a prewashed PD-10 column and eluted with tricine/NO$_3$ buffer. The conjugation ratio and recovery were determined by comparison of the UV-absorption at 280 nm and 550 nm of the protein fractions using a calibration curve of both trastuzumab and Rhodamine-LCL-chloride in tricine/NaNO$_3$ buffer. The average ratio of LCL:mAb was 2.4:1. A portion of the product (510 µg) was radiolabeled with 14.3 MBq 89Zr using published procedures (Verel et al., *Journal of Nuclear Medicine* 2003, 1271-1281) to afford 89Zr-trastuzumab-LCL-Rhodamine. (9.9 MBq, 72% overall yield). Radiochemical purity: TLC (95%), HPLC (100%), SDS-Page (>90%).

Immunoreactivity of 89Zr-trastuzumab-LCL-Rhodamine and 89Zr-trastuzumab

The immunoreactivity of anti-HER289Zr-trastuzumab-LCL-Rhodamine and was determined using 2% paraformaldehyde fixed HER2-expressing SKOV-3 cells and compared to 89Zr-trastuzumab.

As shown in FIG. 2.1 and FIG. 2.2, no loss in immunoreactivity was observed.

FIG. 2.1 shows a binding plot for binding of 89Zr-trastuzumab and 89Zr-trastuzumab-LCL-Rhodamine to HER2-expressing SKOV-3 cells.

FIG. 2.2 shows a Lineweaver Burk plot for binding of 89Zr-trastuzumab and 89Zr-trastuzumab-LCL-Rhodamine to HER2-expressing SKOV-3 cells. Note that binding of anti-HER2 antibody trastuzumab to HER2-expressing SKOV-3 cells has not become affected by coupling of, on average, 2.4 LCL-Rhodamine groups per mAb molecule (maximal antibody binding was not achieved due to lack of HER2 antigen excess in comparison to trastuzumab).

Example 3. Erlotinib-LCL Targeting Complexes

Coupling strategies for preparation of erlotinib-LCL cell-targeting complexes are summarized in Scheme 1.

solution was stored at 4° C. The identity and purity of the product was confirmed by $^{195}$Pt-NMR (DMF-d6): δ −2075 ppm.

Erlotinib.HCl (125 mg, 0.3 mmol) and triethyl amine (88 mg, 0.9 mmol) were dissolved in 37.5 ml of DMF and reacted with LCL-chloride (176 mg, 0.5 mmol, dissolved in 22.5 ml of DMF) at 65° C. for 17 hours. To this mixture, dilute HCl (65 ml, 0.1 mM) was added and subsequently the Scheme 1. Preparation of elotinib-LCL cell targeting complexes.

method 1

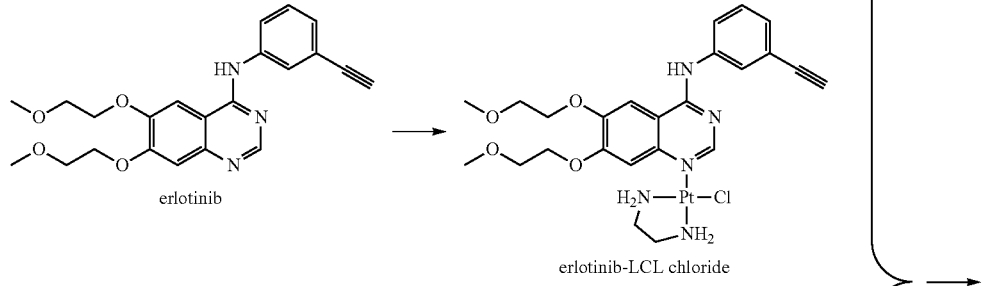

method 2

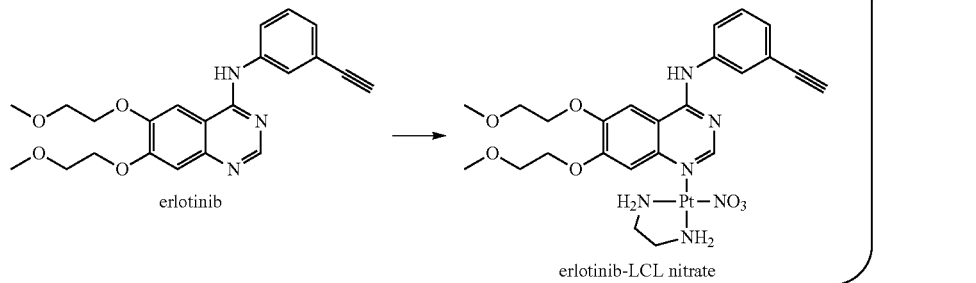

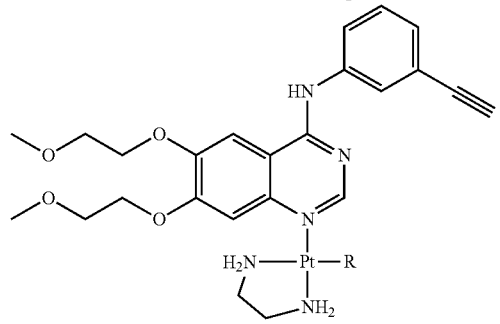

R = cell targeting ligand
(e.g. cetuximab, trastuzumab)
erlotinib-LCL
cell targeting complexes Method 1: Synthesis of erlotinib-LCL-chloride Dichloro(ethylenediamine)platinum(II) (Pt(en)Cl$_2$); 300 mg, 1.76 mmol, dissolved in 30 ml dimethylformamide (DMF)) was converted into Pt(en)(NO$_3$)Cl (LCL-chloride) by adding 1 molar equivalent of AgNO$_3$ (520 mg, 1.76 mmol, dissolved in 52 ml of DMF) divided into four equal portions. Each addition was separated by 2 hours and the mixture was stirred in the absence of light, at ambient temperature. The grey precipitated silver chloride was removed by filtration over a 0.2 µm membrane filter 16 hours after the last addition. The resulting pale yellow solvents were removed under reduced pressure. The crude product was redissolved in MILLI-Q® and purified by preparative HPLC (Phenomenex (P/NO: 00G-4253-P0), Luna 2, 10µ, C18 column, 250×21.20 mm. Eluent A: 90% NaCl (20 mM)/10% isopropanol; Eluent B: 30% NaCl (20 mM)/70% isopropanol, gradient elution (0% B from 0-17.7 minutes; 0-30% B from 17.7-35.3; 30-80% B from 35.3-79.4 minutes; 80-100% B from 79.4-88.2 minutes; 100% B from 88.2-114.7 minutes; 100-0% B from 114.7-123.6 minutes; 0% B from 123.6-158.8 minutes, flow 5.0 mL/minute). Elution buffers were subsequently removed by co-evaporation in vacuo (yield 22%). Erlotinib-LCL-chloride was stored at 4° C. until further use. The identity and purity of the final product erlotinib-LCL-chloride was confirmed by HPLC (>95%), $^{195}$Pt-NMR (DMF-d6): δ −2543 ppm and mass spectroscopy (calculated mass: 684 (m/z); detected: 684 [M+]).

Method 2: Synthesis of erlotinib-LCL-nitrate

LCL-chloride (275 mg, 0.78 mmol, dissolved in 40 ml DMF) was converted into LCL-nitrate Pt(en)(NO$_3$)(NO$_3$) by adding 1 molar equivalent of AgNO3 (123 mg, 0.78 mmol, dissolved in 12 ml of DMF) divided into four equal portions. Each addition was separated by 2 hours and the mixture was stirred in the absence of light, at ambient temperature, in between additions. The grey precipitated silver chloride was removed by filtration over a 0.2 μm membrane filter 16 hours after the last addition. The resulting pale yellow solution was stored at 4° C. The identity and purity of the product was confirmed by $^{195}$Pt-NMR (DMF-d6): δ −1850 ppm.

Erlotinib.HCl (125 mg, 0.291 mmol) was converted in its free base form by adding a three-times molar excess of triethyl amine (88 mg, 0.87 mmol) in 12.5 ml of DMF. The mixture was stirred for 2 hours at room temperature, after which the solvent was removed under reduced pressure. The product was washed three times with 5 ml MILLI-Q® and redissolved in 12.5 ml DMF. Subsequently, 3 ml of this solution was reacted with LCL-nitrate (46 mg, 0.12 mmol, dissolved in 9 ml of DMF) at 65° C. for 17 hours. To this mixture, 40 ml of MILLI-Q® was added and subsequently the solvent was removed under reduced pressure. The crude product was redissolved in MILLI-Q® and purified by preparative HPLC (Phenomenex (P/NO: 00G-4253-P0), Luna 2, 10μ, C18 column, 250×21.20 mm. Eluent A: 90% NaCl (20 mM)/10% isopropanol; Eluent B: 30% NaCl (20 mM)/70% isopropanol, gradient elution (0% B from 0-17.7 minutes; 0-30% B from 17.7-35.3; 30-80% B from 35.3-79.4 minutes; 80-100% B from 79.4-88.2 minutes; 100% B from 88.2-114.7 minutes; 100-0% B from 114.7-123.6 minutes; 0% B from 123.6-158.8 minutes, flow 5.0 mL/minute). Elution buffers were subsequently removed by co-evaporation in vacuo (yield 29%). Erlotinib-LCL-nitrate was stored at 4° C. until further use. The identity and purity of the final product erlotinib-LCL-nitrate was confirmed by HPLC (>95%), $^{195}$Pt-NMR (DMF-d6): δ −2525 ppm and mass spectroscopy (calculated mass: 683 (m/z); detected: 683 [M+]).

Coupling of Erlotinib-LCL to Cell-Targeting Moieties

A general protocol was developed for coupling of erlotinib-LCL (either erlotinib-LCL-chloride or erlotinib-LCL-nitrate) to cell-targeting moieties. Typical examples of synthesis protocols at different coupling ratios are given below. When applicable for the performed assays, aliquots of radiolabeled targeting moiety were spiked to the targeting moiety, to enable tracing of the cell-targeting complex via the radiotracer moiety.

Cetuximab-LCL-erlotinib

Cetuximab (1.5 mg, 16.7 μM) was reacted with erlotinib-LCL at different molar amounts corresponding to 5-50 times excess in a 20 mM tricine/NO$_3$ buffer at pH 8.5 at 37° C. for 1 hour. Products were purified by size-exclusion chromatography on PD10 columns. The number of conjugated LCL-groups was determined by UV measurement on a Nanodrop.

Radiolabeled erlotinib-LCL-cetuximab was prepared by reacting erlotinib-LCL with 1.5 mg cetuximab spiked with 200 μl of 131I-cetuximab (10 MBq).

Trastuzumab-LCL-erlotinib

Trastuzumab-LCL-erlotinib was prepared according to the same procedures.

Radiolabeling of Cetuximab and Trastuzumab

250 μg cetuximab was labeled with 15 MBq $^{124}$I, according to standard procedures. In short, in a reaction vial, coated with 25 μg of Iodogen, 250 μg cetuximab and $^{124}$I (pre-incubated with 50 μl NaI (10 μg/ml)) in a phosphate buffer was added. After 4 minutes, the reaction was stopped with ascorbic acid and the reaction mixture was purified via a prewashed PD-10 column. Yield was 89.5%, while radiochemical purity was 99.9%.

250 μg cetuximab was labeled with 60 MBq $^{131}$I, according to standard procedures. In short, in a reaction vial, coated with 25 μg of Iodogen, 250 μg cetuximab and $^{131}$I in a phosphate buffer was added. After 4 minutes, the reaction was stopped with ascorbic acid and the reaction mixture was purified via a prewashed PD-10 column. Yield was 75.6%, while radiochemical purity was 99.9%.

Trastuzumab was radiolabeled according to the same procedures.

Binding Assays

The binding assay for cetuximab was performed with EGFR1-expressing A431 tumor cells. First, the A431 cells were washed in PBS containing 1% BSA and a serial dilution of cells was made, the highest concentration was 1.7×10$^6$/ml. As a control, an excess of unlabeled cetuximab was added to one tube. At all tubes, including the control tube, 16 ng/ml $^{131}$I-cetuximab-LCL-erlotinib was added. After overnight incubation at 4° C., the cells were spun down and pellet and supernatant were counted in a gamma-counter and percentage of bound and free radioactivity were measured. FIG. 3.1 shows the results of these binding assays. In red, the binding of unconjugated cetuximab is shown; the blue lines represent the different cetuximab- LCL-erlotinib conjugates. Note that binding of cetuximab-LCL-erlotinib to EGFR-expressing A431 cells has not become substantially affected upon reaction with up to 15 LCL-erlotinib groups per mAb molecule.

For binding studies with trastuzumab, HER-2-expressing SKOV-3 cells (Ovarian cancer) were used. After washing, a serial dilution of SKOV-3 cells was made with $0.5 \times 10^6$ cells/ml as highest concentration. As a control, an excess of unlabeled trastuzumab was added to one tube. At all tubes, including the control tube, 200 ng/ml $^{131}$I-trastuzumab-LCL-erlotinib was added. After overnight incubation at 4° C., the cells were spun down and pellet and supernatant were counted in a gamma-counter and percentage of bound and free radioactivity were measured.

FIG. 3.2 shows the results of these binding assays. In red, the binding of unconjugated trastuzumab to SKOV-3 cells is shown; the blue lines represent the different cetuximab-LCL-trastuzumab conjugates. Note that binding of trastuzumab-LCL-erlotinib to HER2-expressing SKOV-3 cells has not become substantially affected upon reaction with up to 25 LCL-erlotinib groups per mAb molecule. All these data indicate that the integrity of cetuximab and trastuzumab is still preserved even after performing conjugation with 25 erlotinib-LCL groups.

Animal Study

In an animal study, performed in nude mice (HSD: Athymic Nude-Foxn1nu, Harlan) subcutaneously implanted with human xenografts of the vulvar tumor line A431 at two lateral sides, blood kinetics and biodistribution of cetuximab and cetuximab-LCL-erlotinib were compared.

To this end, six mice were intra orbitally (i.o.) co-injected with 0.37 MBq $^{131}$I-cetuximab-LCL-erlotinib (modified with 13 erlotinib-LCL groups) and 0.37 MBq $^{124}$I-cetuximab with 500 μg cetuximab in total per mouse. Another six mice were i.o. co-injected with 0.37 MBq $^{131}$I-cetuximab-LCL-erlotinib (modified with 22 LCL groups) and 0.37 MBq $^{124}$I-cetuximab with 500 μg cetuximab in total per mouse. Blood samples were drawn at 24, 48, 72, 96 and 168 hours post injection (p.i.) and biodistribution was performed after 72 and 168 hours p.i. Blood and biodistribution samples were counted in gamma counter and % ID/g were calculated.

Blood kinetics of cetuximab and cetuximab-LCL-erlotinib were comparable up to 168 hours p.i. For both groups of mice, the observed plasma concentration profile of $^{131}$I-cetuximab-LCL-erlotinib matched to the corresponding reference profile of $^{124}$I-cetuximab. Clearly, also in vivo, it was shown that due to the mild reaction conditions, the targeting moiety, cetuximab, kept most of its pharmacokinetic behavior (see FIG. 3.3).

FIG. 3.1 shows binding plots of cetuximab and cetuximab-LCL-erlotinib with A431 cells. Note that binding of cetuximab-LCL-erlotinib to EGFR1-expressing A431 cells has not become substantially affected upon reaction with up to 15 LCL-erlotinib groups per mAb molecule.

FIG. 3.2 shows binding plots of trastuzumab and trastuzumab-LCL-erlotinib with SKOV-3 cells. Note that binding of trastuzumab-LCL-erlotinib to HER2-expressing SKOV-3 cells has not become substantially affected upon reaction with up to 25 LCL-erlotinib groups per mAb molecule.

FIG. 3.3 shows blood kinetics of $^{124}$I-cetuximab and $^{131}$I-cetuximab-LCL-erlotinib in nude mice bearing A431 xenografts.

Example 4. IRDye800CW-LCL Targeting Complexes

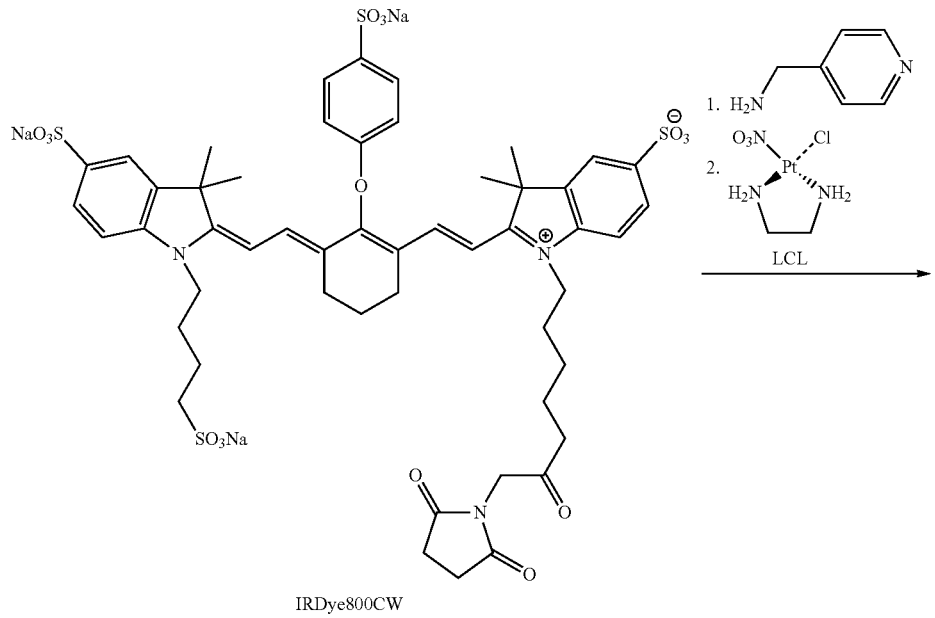

IRDye800CW

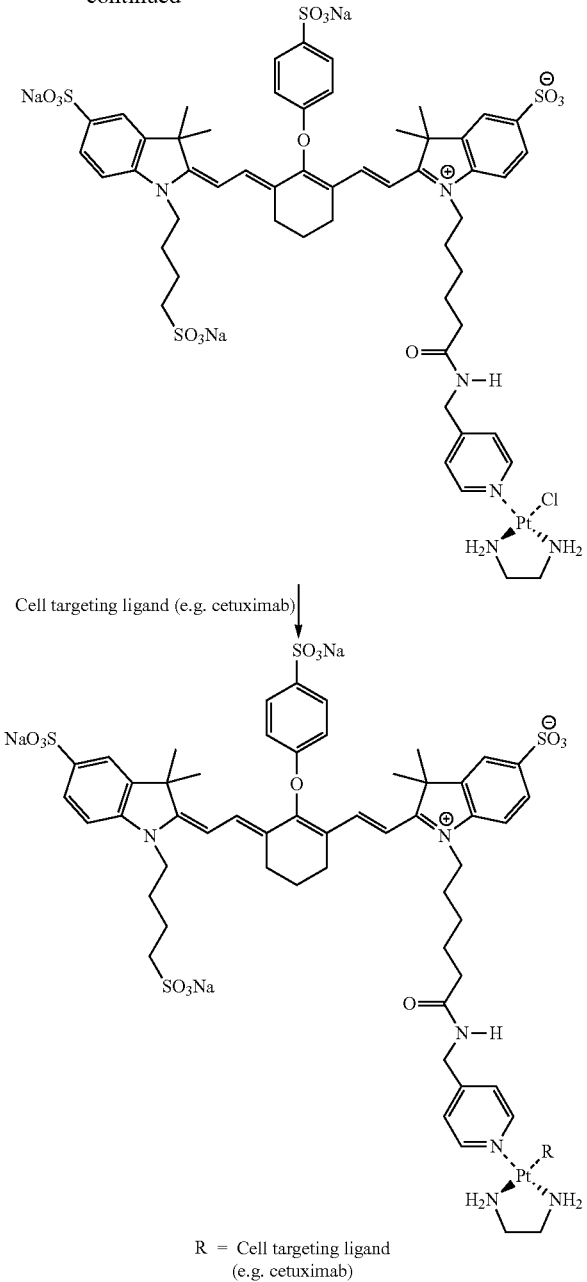

R = Cell targeting ligand
(e.g. cetuximab)

Synthesis of IRDye800CW-LCL-chloride

The NHS ester group of IRDye800CW NHS ester was converted into a LCL compatible moiety via reaction with 4-(methylamine)pyridine (4-py). In a typical example, the pH of a solution of 4-py in MILLI-Q® (10 g/ml) was adjusted to 8.5 by adding small quantities of 37% HCl. Subsequently, to 130 µl of this mixture, 65 µl sodium phosphate buffer solution (pH 8.5) was added followed by 130 µl MILLI-Q®. This solution was then reacted with IRDye800CW NHS ester (12.7 mg, 10.9 µmol, dissolved in 1.3 ml of DMF). The reaction mixture was stirred under the protection of light at ambient temperature for 2 hours. Subsequently, 0.13 ml of this solution was reacted with a four-times excess of LCL-chloride (1.2 mg, 3.5 µmol dissolved in 171 µl DMF) at ambient temperature for 16 hours. The crude product was purified by solid phase extraction (Supelco Supel™-Select HLB SPE column). IRDye800CW-LCL-chloride (Yield: 65%) was stored at 4° C. until further use. The identity and purity of the final product IRDye800CW-LCL-chloride was confirmed by HPLC (>90%).

Coupling of IRDye800CW-LCL-chloride to Cell-Targeting Moieties

As a typical example for preparation of cell-targeting complexes, IRDye800-LCL-Chloride was coupled to trastuzumab or cetuximab. IRDye800CW-LCL-chloride was conjugated to cetuximab by adding 85 µl of IRDye800CW- LCL-Chloride solution (2.3 mg/ml in water, 0.13 µmol IRDye800CW-LCL-Chloride) to a mixture of 200 µl of a cetuximab solution (5 mg/ml in buffer, 1.4 nmol cetuximab), 40 µl of a 250 mM tricine/NaNO$_3$ buffer solution (pH 8.5) and 75 µl MILLI-Q® and the mixture was reacted for 2, 4, 6, 15 and 24 hours at 37° C. The product was purified by PD10 gel filtration. IRDye800CW content was detected on a Spectrostar UV/VIS spectrometer at 780 nm. A calibration curve was constructed using IRDye800CW solutions of known concentrations. Protein content was detected on a Waters 2695 liquid chromatogram equipped with a SUPERDEX® 200 10/300 GL column and a Waters 2695 PDA detector, using PBS as mobile phase. A calibration curve was constructed using protein solutions of known concentrations. Eluting peaks were detected using an absorption wavelength of 280 nm (protein) and 780 nm at the retention time of the mAb (FIG. 4.1), confirming the coordination of IRDye800CW to mAb via the LCL linker.

FIG. 4.1 shows GPC chromatograms of IRDye800CW-LCL-cetuximab.

After 6 hours, 70% of IRDye800CW-LCL-chloride has coupled as compared to the amount that can be coupled after 24 hours (FIG. 4.2). Moreover, after 6 hours, the protein started to precipitate and only 40-50% mAb was recovered.

FIG. 4.2 shows conjugation of IRDye800CW-LCL to mAb (closed symbols) and mAb recovery (open symbols) as a function of time (■ cetuximab ● trastuzumab). The conjugation after 24 hours was taken as 100%.

Example 5. Doxorubicin-LCL Targeting Complexes

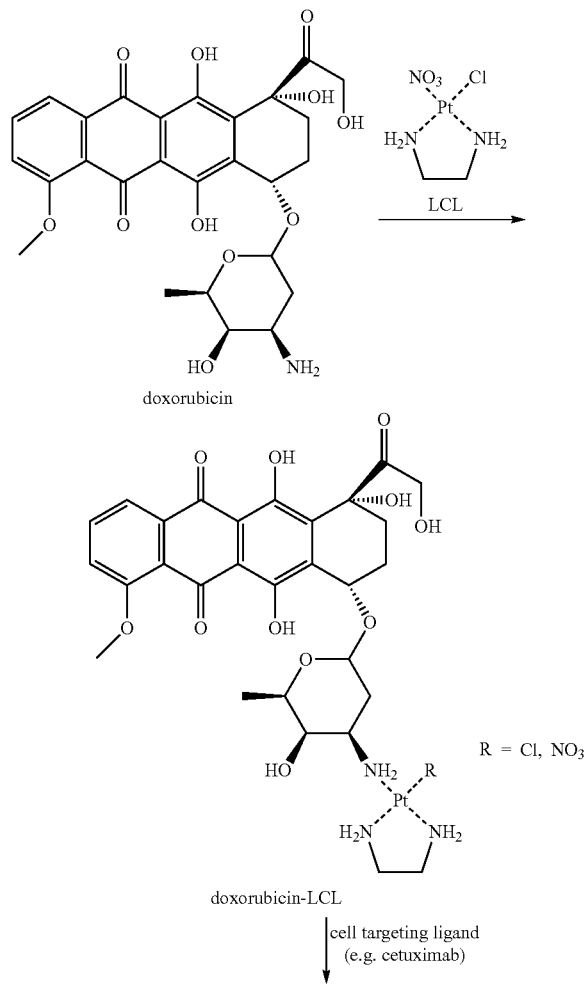

doxorubicin doxorubicin-LCL

R = Cl, NO$_3$ cell targeting ligand (e.g. cetuximab)

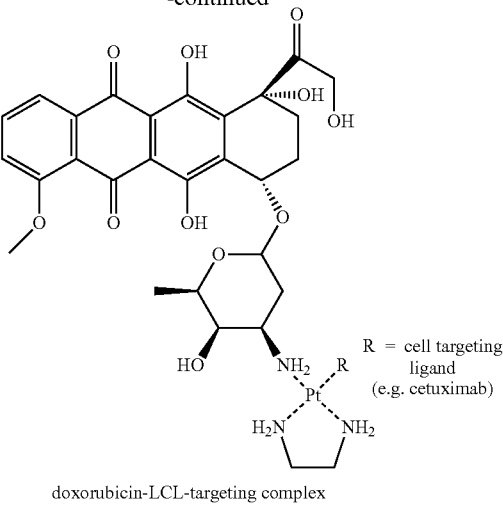

doxorubicin-LCL-targeting complex

R = cell targeting ligand (e.g. cetuximab)

Synthesis of Doxorubicin-LCL Chloride

Doxorubicin (DOX, 5.0 mg, 8.6 mmol, dissolved in 1 ml of water) was reacted with cis-Pt(ethylenediamine)nitrate-chloride (LCL, 30 mg, 86 mmol, dissolved in 4.5 ml of DMF) at 60° C. for 4 days. Purification of DOX-LCL was performed via solid phase extraction (SPE) using Supelco Supel-Select HLB SPE Tubes. The reaction mixture was diluted 40-fold with water and brought onto SPE columns. Unreacted LCL was removed by washing with excess water. DOX-LCL was subsequently eluted with a mixture of acetonitrile and methanol (1/1 v/v). Solvents were removed by rotary evaporation and DOX-LCL was redissolved in water to a concentration of 1.4 mg/ml. The identity and purity of DOX-LCL were confirmed by HPLC (>95%), NMR and mass spectroscopy. The DOX-LCL solution was stored at 4° C. until further use.

Yield: 1.4 mg (1.7 µmol, 20%).

DOX-LCL $^{195}$Pt-NMR (D$_2$O); δPt −2595 ppm (N$_3$—Cl coordination at the NH$_2$ group of DOX).

DOX-LCL ionspray MS: calculated mass 833. Detected 834 m/z [M+H$^+$].

Synthesis of Doxorubicin-LCL-cetuximab

DOX-LCL was conjugated to cetuximab by adding 80 µl of DOX-LCL solution (1.4 mg/ml in water, 0.13 mmol DOX-LCL) to 200 µl of a cetuximab solution (5 mg/ml in buffer, 6.9 nmol cetuximab). 50 µl of a 250 mM tricine/NaNO$_3$ buffer solution (pH 8.5) and 170 µl MILLI-Q® water were added and the mixture was reacted for 1, 5 or 24 hours at 37° C. Unreacted DOX-LCL was removed by PD10 size-exclusion chromatography. The DOX-LCL-cetuximab solution was stored at −20° C. until further use.

The DOX-LCL-cetuximab conjugate was characterized for protein and drug content by UV/VIS spectroscopy and by GPC. DOX content was detected on a Spectrostar UV/VIS spectrometer at 490 nm. A calibration curve was constructed using DOX solutions of known concentrations. GPC analyses were performed on a Waters 2695 liquid chromatograph equipped with a SUPERDEX® 200 10/300GL column, a Waters 2475 fluorescence detector and a Waters 2487 UV detector. PBS was used as a mobile phase. Eluting peaks were detected using excitation and emission wavelengths, respectively, of 280 nm and 330 nm (protein) or an absorption wavelength of 490 nm (DOX). A calibration curve was constructed using protein solutions of known concentrations.

As shown in FIG. 5.1, DOX-LCL was rapidly complexed to cetuximab, with already 67% of the maximum conjugation after 1 hour at 37° C. and 90% coupling after 5 hours of reaction at 37° C. After 24 hours of reaction, some protein precipitation was observed. This precipitation was not yet observed after 1 hour of reaction, which emphasizes that a short reaction time of 60 minutes is most preferred.

FIG. 5.1 shows conjugation of DOX-LCL to cetuximab as a function of time. The conjugation after 24 hours was taken as 100%.

GPC size-exclusion chromatography confirmed the stable conjugation of DOX-LCL to cetuximab, as shown in FIG. 5.2. The doxorubicin-specific signal at 490 nm eluted at the retention time of cetuximab, confirming the stable coordination of DOX to cetuximab via the LCL linker.

FIG. 5.2 shows GPC chromatograms of DOX-LCL-cetuximab.

Synthesis of doxorubicin-LCL-trastuzumab

DOX-LCL was conjugated to trastuzumab by adding 90 µl of DOX-LCL solution (2.7 mg/ml in water, 0.28 µmol DOX-LCL) to 100 µl of a trastuzumab solution (21 mg/ml in buffer, 14 nmol trastuzumab). 25 µl of a 250 mM tricine/$NaNO_3$ buffer solution (pH 8.5) and 35 µl MILLI-Q® water were added and the mixture was reacted for 24 hours at 37° C. Unreacted DOX-LCL was removed by size-exclusion chromatography using disposable PD10 columns (GE Healthcare). The DOX-LCL-trastuzumab solution was stored at −20° C. until further use.

Characterization of DOX-LCL-trastuzumab was similar to characterization of DOX-LCL-cetuximab as described earlier.

DOX-LCL-trastuzumab contained, on average, 2.2 coupled DOX molecules per protein molecule, as calculated from its protein and drug content.

Functional Evaluation of doxorubicin-LCL-cetuximab and doxorubicin-LCL-trastuzumab A431 cells were cultured in Dulbecco's Modified Eagle's medium (DMEM, PAA, Pasching, Austria) containing 3.7 g/l sodium bicarbonate, 4.5 g/l 1-glucose, 2 mM 1-glutamine and supplemented with 7.5% (v/v) fetal bovine serum, penicillin (100 IU/ml), streptomycin (100 µg/ml), and amphotericin B (0.25 µg/ml) at 37° C. in a humidified atmosphere containing 5% $CO_2$. 4000 cells/well were seeded into 96-well plates. After 24 hours, medium was replaced by fresh medium spiked with DOX-LCL-antibody diluted in PBS in final concentrations of 25 nM–6.7 µM at least in triplicate. To determine the total cell number, cellular proteins were precipitated by the addition of trichloroacetic acid to 4% after 1 day of growth. Cells were washed with water, dried at RT and stained with 0.4% sulforhodamine B in 1% acetic acid for 30 minutes. Excess dye was washed away with 1% acetic acid and cells were dried at RT. Bound dye was extracted with unbuffered 10 mM Tris for 15 minutes and OD values were measured at 510 nm with a Bio-Rad Novapath Microplate Reader (Bio-Rad Laboratories, Veenendaal, The Netherlands).

FIG. 5.3 clearly shows that DOX-LCL-antibody conjugates are more effective in killing cells than the unmodified antibodies. The effect of DOX-LCL-cetuximab is similar to that of DOX without a targeting moiety (FIG. 5.3A). It should be noted that A431 cells display mainly EGFR receptors (targeted by cetuximab) and a relatively small amount of HER2 receptors (targeted by trastuzumab) at their cell membrane. Nevertheless, at the highest concentration of 7 µM, a significant effect of DOX-LCL-trastuzumab compared to unmodified trastuzumab is observed (FIG. 5.3B).

FIG. 5.3 shows the effect of DOX-LCL-cetuximab (A) and DOX-LCL-trastuzumab (B) conjugates on A431 cell viability. Non-treated cells are set as 100%. Data are presented as mean±standard deviation (experiments performed in triplicate).

Example 6. Paclitaxel-LCL Targeting Complexes

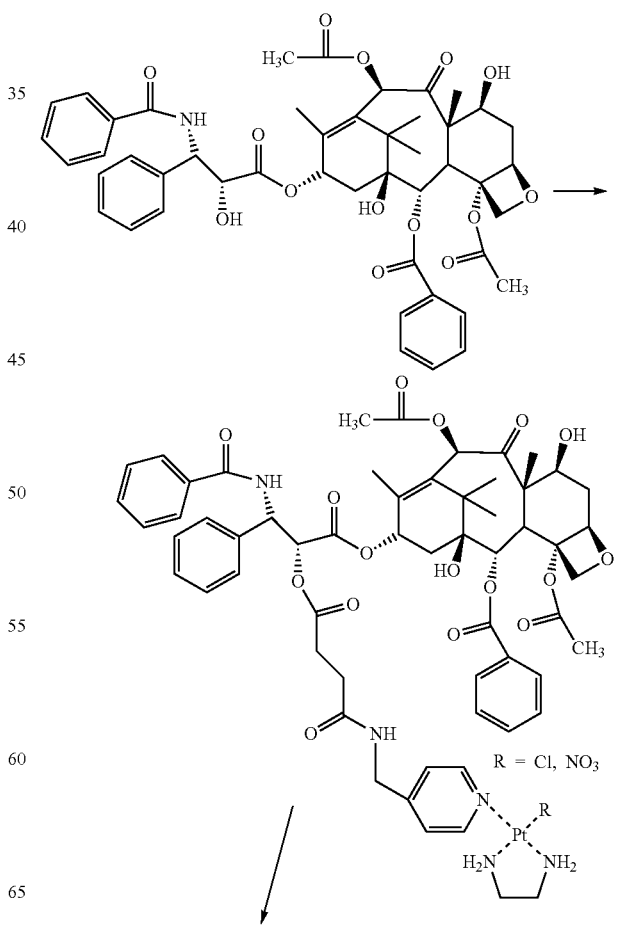

R = Cl, $NO_3$

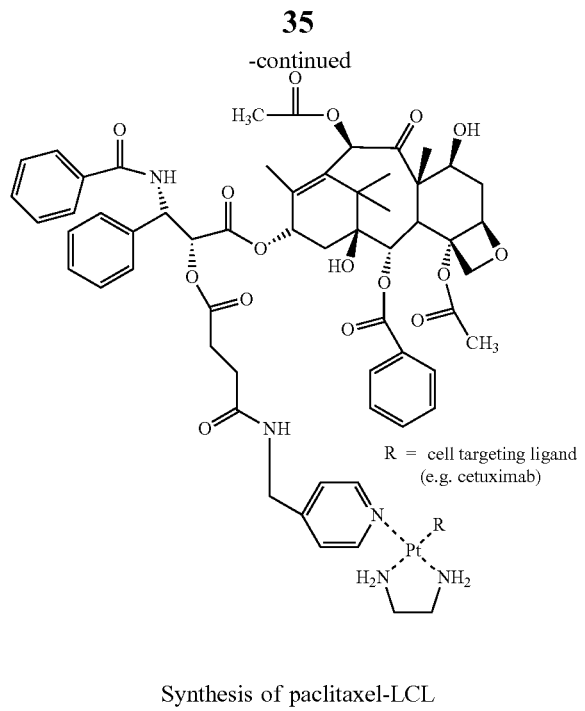

Synthesis of paclitaxel-LCL

Paclitaxel (PAX, 280 mg, 0.33 mmol) was dissolved in 7 ml of dry pyridine. Succinic anhydride (393 mg, 3.9 mmol) was added and the mixture was reacted at room temperature for 5 hours in the presence of molecular sieves. The pyridine was evaporated under reduced pressure and the residue was redissolved in 2 ml of DMSO. This solution was precipitated in a large excess of water. Subsequently, the precipitate was filtered off and dried under reduced pressure in the presence of phosphorous pentoxide. In the $^1$H NMR spectrum (DMSO-$d_6$) of the product, a signal appeared at 2.62 ppm corresponding to the succinic methylene protons, confirming the formation of succinyl-PAX.

In the second step of the synthesis procedure, succinyl-PAX (108 mg, 0.11 mmol) was dissolved in 2 ml of dichloromethane, together with N,N'-dicyclohexylcarbodiimide (41 mg, 0.20 mmol). N-hydroxysuccinimide (18 mg, 0.16 mmol) was added and the mixture was allowed to react for 18 hours at room temperature in the presence of molecular sieves. The reaction mixture was filtered using a 0.45 μm syringe filter and precipitated in a large excess of a cold mixture of diethyl ether and methanol (20/1 v/v). NHS-succinyl-paclitaxel was obtained by filtration and dried under vacuum. In the $^1$H NMR spectrum (DMSO-$d_6$), the succinic methylene protons shifted downfield and a new peak appeared at 2.79 ppm corresponding to the succinimide protons, confirming the conversion of the carboxylic acid group into its N-hydroxysuccinimide active ester.

In the third step, 200 μl of a NHS-succinyl-PAX solution (5 mg/ml in DMF, 1.0 mmol NHS-succinyl-paclitaxel) was mixed with 20 μl of a 4-picolylamine solution (5 mg/ml in DMF, 1.0 mmol 4-picolylamine). The mixture was reacted for 48 hours at room temperature. The identity and purity of picolyl-PAX were confirmed by HPLC (>95%) and ionspray MS (calculated mass 1044; detected 1044 m/z).

In the final step of the procedure, picolyl-PAX (50 μg, 48 nmol, dissolved in 10 μA of DMF) was reacted with LCL (84 μs, 0.24 μmol, dissolved in 12 μl of DMF) at 60° C. for 48 hours. The identity and purity of picolyl-PAX-LCL were checked by HPLC (>80%) and mass spectroscopy. The picolyl-PAX-LCL solution was stored at 4° C. until further use.

Picolyl-PAX-LCL ionspray MS: calculated mass 1334. Detected 1334 m/z.

The procedure for coupling of picolyl-PAX-LCL to targeting moieties is analogous to the procedure described above for coupling of doxorubicin-LCL to targeting moieties.

Example 7. DM1-LCL Targeting Complexes

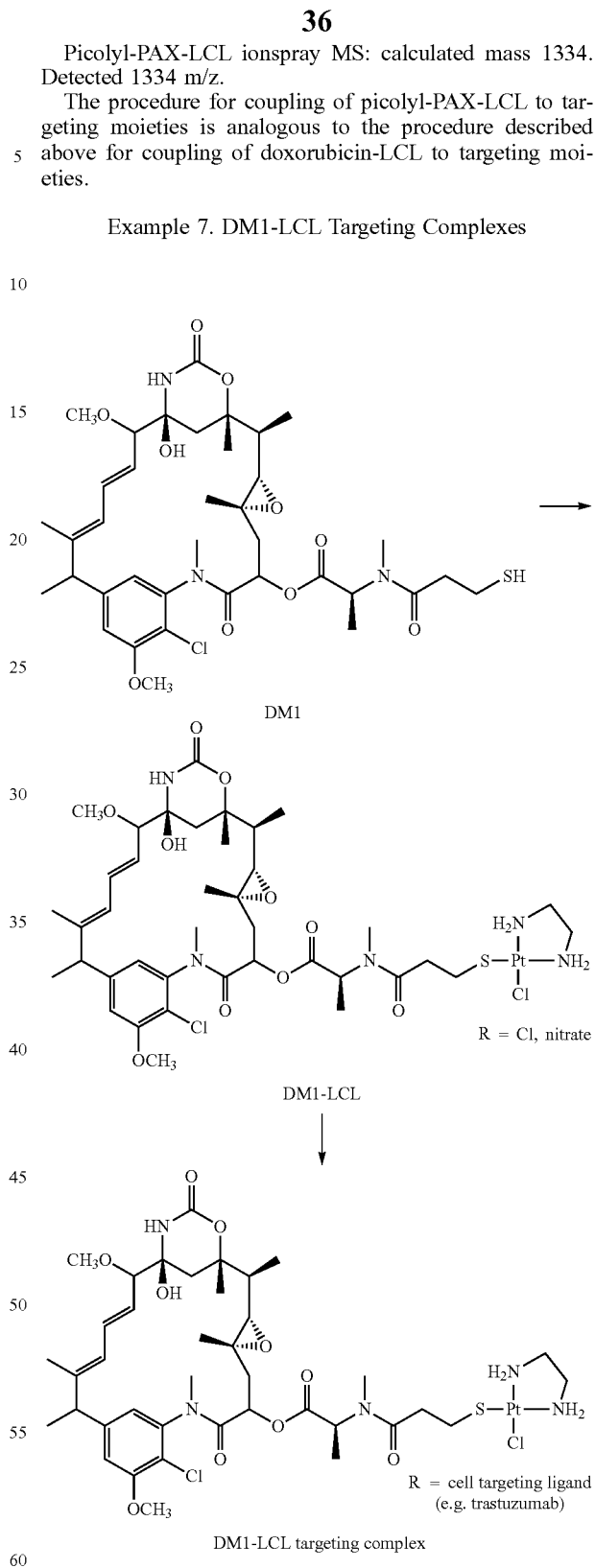

The procedure for coupling of DM1 to LCL is analogous to the procedure described above for coupling of doxorubicin to LCL. Also, the procedure for coupling of DM1-LCL to targeting moieties is analogous to the procedure described above for coupling of doxorubicin-LCL to targeting moieties.

The invention claimed is:

1. A method for preparing a cell-targeting conjugate by coupling erlotinib or an auristatin to a targeting moiety, the method comprising:
   i. providing a platinum(II)ethlyenediamine compound, either as Pt(en)Cl$_2$ or as Pt(en)(NO$_3$)$_2$, having a first reactive group and a second reactive group, wherein the first reactive group and the second reactive group are NO$_3$ or Cl of the platinum(II)ethlyenediamine compound;
   ii. providing at least one functional moiety, which is erlotinib or an auristatin;
   iii. mixing said platinum(II)ethlyenediamine compound with the functional moiety, wherein the first reactive group reacts with said functional moiety, thereby forming a functional metal ion construct,
   iv. mixing functional metal ion construct(s) with a targeting moiety selected from the group consisting of adalimumab, bevacizumab, catumaxomab, cetuximab, gemtuzumab, golimumab, infliximab, panitumumab, rituximab, and trastuzumab, such that the second reactive group forms a coordination bond with the targeting moiety such that a conjugate is formed and wherein the immunoreactivity of the targeting moiety of said conjugate remains substantially the same as the immunoreactivity of the unbound targeting moiety; and
   v. separating the resulting conjugate from the mixture.

2. The method according to claim 1, wherein functional metal ion constructs are mixed with the targeting moiety or moieties for from 10 to 240 minutes.

3. The method according to claim 1, wherein the mixing is carried out at a temperature of from 20 to 50° C.

4. The method according to claim 1, wherein before or during mixing, the pH of the mixture of the functional metal ion constructs and the targeting moiety or moieties is adjusted to from 4 to 12.

5. The method according to claim 1, wherein at least one functional metal ion construct is bound via a coordination bond with one targeting moiety.

6. The method according to claim 1, wherein 1-30 functional metal ion constructs are bound via a coordination bond with one targeting moiety.

7. A method of preparing a conjugate, the method comprising:
   (a) mixing platinum complex platinum(II)ethylenediamine Pt(en)(NO$_3$)$_2$, with a functional moiety selected from the group consisting of erlotinib and an auristatin, so as to form a metal ion construct;
   (b) mixing the thus formed metal ion construct with a targeting moiety selected from the group consisting of adalimumab, bevacizumab, catumaxomab, cetuximab, gemtuzumab, golimumab, infliximab, panitumumab, rituximab, and trastuzumab to form a conjugate; and
   (c) separating the conjugate from the mixture.

* * * * *